（12) United States Patent
Noji et al.

(10) Patent No.: US 10,471,429 B2
(45) Date of Patent: Nov. 12, 2019

(54) HIGH-DENSITY MICROCHAMBER ARRAY AND MANUFACTURING METHOD THEREOF

(71) Applicant: THE UNIVERSITY OF TOKYO, Tokyo (JP)

(72) Inventors: Hiroyuki Noji, Tokyo (JP); Rikiya Watanabe, Tokyo (JP); Hiroaki Suga, Tokyo (JP); Daishi Fujita, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 538 days.

(21) Appl. No.: 14/913,470

(22) PCT Filed: Aug. 18, 2014

(86) PCT No.: PCT/JP2014/071585
§ 371 (c)(1),
(2) Date: May 5, 2016

(87) PCT Pub. No.: WO2015/025822
PCT Pub. Date: Feb. 26, 2015

(65) Prior Publication Data
US 2016/0296928 A1 Oct. 13, 2016

(30) Foreign Application Priority Data
Aug. 21, 2013 (JP) ................................. 2013-171493

(51) Int. Cl.
*B01L 3/00* (2006.01)
*B01J 19/00* (2006.01)
*G01N 33/487* (2006.01)

(52) U.S. Cl.
CPC ......... *B01L 3/5085* (2013.01); *B01J 19/0046* (2013.01); *B01L 3/502769* (2013.01);
(Continued)

(58) Field of Classification Search
CPC .................. B01L 2300/0819; B01J 2219/0061
(Continued)

(56) References Cited

U.S. PATENT DOCUMENTS

2003/0148401 A1* 8/2003 Agrawal ............. B01J 19/0046
506/9
2007/0161101 A1 7/2007 Takeuchi

FOREIGN PATENT DOCUMENTS

EP          2219032 A1    8/2010
JP     2006-312141 A    11/2006
(Continued)

OTHER PUBLICATIONS

Mar. 1, 2017 Search Report issued in European Patent Application No. 14838020.7.
(Continued)

*Primary Examiner* — Natalia Levkovich
(74) *Attorney, Agent, or Firm* — Oliff PLC

(57) ABSTRACT

A material film is formed as a thin film having a thickness of 1 μm on a surface of a glass substrate. A plurality of micro-chambers having a diameter of 5 μm are formed in the material film to be arrayed at a high density. The respective chambers filled with an aqueous test solution have openings that are liquid-sealed by a lipid bilayer membrane to provide a high-density micro-chamber array. Significant downsizing of the micro-chambers enhances a change in concentration by a reaction of one biomolecule in the chamber and thereby increases the detection sensitivity. In the configuration that a large number of micro-chambers are formed at a high density, even in the case of an extremely slow reaction of the biomolecule, the reaction proceeds in any of the chambers. This configuration accordingly enables the reaction of the biomolecule to be detected with high sensitivity.

9 Claims, 10 Drawing Sheets

(52) U.S. Cl.
CPC ............... *G01N 33/48721* (2013.01); *B01J 2219/00317* (2013.01); *B01J 2219/00331* (2013.01); *B01J 2219/00662* (2013.01); *B01J 2219/00725* (2013.01); *B01J 2219/00734* (2013.01); *B01L 2200/0689* (2013.01); *B01L 2200/12* (2013.01); *B01L 2300/0819* (2013.01); *B01L 2300/0861* (2013.01); *B01L 2300/0893* (2013.01); *B01L 2300/0896* (2013.01); *B01L 2300/165* (2013.01)

(58) Field of Classification Search
USPC .................................................. 422/552, 603
See application file for complete search history.

(56) References Cited

FOREIGN PATENT DOCUMENTS

| | | |
|---|---|---|
| JP | 2012-081405 A | 4/2012 |
| JP | 2012-205537 A | 10/2012 |
| WO | 2005/071405 A1 | 8/2005 |

OTHER PUBLICATIONS

Joon S. Shim et al. "Formation of Lipid Bilayers Inside Microfluidic Channel Array for Monitoring Membrane-Embedded Nanopores of PHI29 DNA Packaging Nanomotor". Biomedical Microdevices, Kluwer Academic Publishers, vol. 14, No. 5, Jul. 7, 2012, pp. 921-928.

Nov. 18, 2014 International Search Report issued in International Patent Application No. PCT/JP2014/071585.

Aug. 13, 2015 International Preliminary Report on Patentability issued in International Patent Application No. PCT/JP2014/071585.

Nov. 18, 2014 Written Opinion issued in Interntional Patent Application No. PCT/JP2014/071585.

Tonooka et al; "Lipid bilayer on a droplet: formation of lipid bilayers on a droplet array;" Tech Dig IEEE Micro Electro Mech Syst; 2012; vol. 25; No. 2; pp. 1049-1052.

Watanabe et al; "Electrical recording of nanopore membrane proteins in a microfluidic device;" The papers of Technical Meeting on Bio Micro Systems; IEE Japan; 2010; vol. BMS-10; No. 7-27; pp. 5-8.

Hansen et al; Large scale biomimetic membrane arrays; Anal Bioanal Chem; 2009; vol. 395; No. 3; pp. 719-727.

\* cited by examiner

HIGH-DENSITY MICROCHAMBER ARRAY AND MANUFACTURING METHOD THEREOF

TECHNICAL FIELD

The present invention relates to a high-density micro-chamber array and manufacturing method thereof, and more specifically relates to a high-density micro-chamber array having micro-chambers formed on a surface of a flat substrate at a high density and a manufacturing method of such a high-density micro-chamber array.

BACKGROUND ART

A proposed technique supplies a lipid bilayer membrane-forming lipid solution into two wells that are separated from each other across a partition having through holes of 500 nm to 500 μm in pore diameter, adds water or an aqueous solution to the respective wells to form droplets of water or the aqueous solution in the lipid solution and leaves the wells in this state to form a lipid bilayer membrane in the through holes of the partition (see, for example, Patent Literature 1).

Another proposed technique provides chambers and microchannels on a surface and a rear face of a substrate, provides micropores that pass through the chambers and the microchannels, introduces a buffer medium into the chambers, sequentially supplies the buffer medium, a lipid-containing organic solvent and the buffer medium into the microchannels, applies a pressure to the buffer medium in the chambers to adjust the internal pressure of the chambers, and forms a thin lipid plane membrane in the micropores as a lipid bilayer membrane (see, for example, Patent Literature 2).

CITATION LIST

Patent Literature

PTL 1: JP 2012-81405A
PTL 2: JP 2006-312141A

SUMMARY OF INVENTION

In various reactions of biomolecules proceeding via a lipid bilayer membrane, for example, membrane transport, membrane transmission reaction or enzyme reaction on the surface of a membrane, it takes a longtime to diffuse a reaction product or there is an extremely slow change in material concentration accompanied by the enzyme activity. In the case of forming reaction vessels (chambers) by employing the above method of forming the lipid bilayer membrane, the chamber has a large capacity, and there is a difficulty in forming a large number of chambers simultaneously. This results in a failure to detect the various reactions of biomolecules proceeding via the lipid bilayer membrane with high sensitivity. The large capacity of the chamber provides a small change of concentration in the chamber and leads to a difficulty in detection as a change of concentration. The small number of chambers causes the reaction not to proceed in any of the chambers, due to the extremely slow reaction of a biomolecule. There is accordingly a need for a high-density micro-chamber array in which a large number of chambers of the extremely small capacity that are liquid-sealed by a lipid bilayer membrane are formed at a high density.

With regard to the high-density micro-chamber array and the manufacturing method thereof, an object of the invention is to provide a high-density micro-chamber array in which a large number of chambers of the extremely small capacity that are liquid-sealed by a lipid bilayer membrane are formed at a high density, and to provide a manufacturing method of such a high-density micro-chamber array.

In order to attain at least part of the above and the other related objects, a high-density micro-chamber array and manufacturing method thereof of the invention has the configurations discussed below.

The present invention is directed to a first high-density micro-chamber array. The first high-density micro-chamber array includes a flat substrate, a plurality of micro-chambers, each having a capacity of not greater than $4000 \times 10^{-18}$ m$^3$, that are formed from a hydrophobic material on a surface of the substrate to be arrayed regularly at a high density and a lipid bilayer membrane that is formed at openings of the plurality of micro-chambers filled with an aqueous test solution to liquid-seal the aqueous test solution.

In the first high-density micro-chamber array of this aspect, the plurality of micro-chambers, each having the capacity of not greater than $4000 \times 10^{-18}$ m$^3$, are formed on the surface of the flat substrate to be arrayed regularly at a high density. The openings of the respective micro-chambers filled with the aqueous test solution are liquid-sealed by the lipid bilayer membrane. In the first high-density micro-chamber array, a large number of chambers of the extremely small capacity that are liquid-sealed by the lipid bilayer membrane are accordingly formed at a high density. In an application of the first high-density micro-chamber array of this aspect for detection of the reaction of a biomolecule, reducing the capacity of the micro-chambers to be not greater than $4000 \times 10^{-18}$ m$^3$ decreases the number of biomolecules in each micro-chamber. This results in enhancing a change in concentration in the chamber by a reaction of one biomolecule and increasing the detection sensitivity in detection as the change in concentration. Even in the case of an extremely slow reaction of the biomolecule, this enables the reaction of the biomolecule to be detected with high sensitivity. In the array configured to have a large number of micro-chambers formed at a high density, even when the reaction of the biomolecule occurs at a low frequency, the reaction proceeds in any of the chambers. This accordingly enables the reaction of the biomolecule to be detected with high sensitivity. The capacity of the micro-chamber is determined according to the magnitude of a reaction rate of a biomolecule specified as a test object and the content rate of the biomolecule and is preferably not greater than $4000 \times 10^{-18}$ m$^3$ for the biomolecule having the high reaction rate and preferably not greater than $1000 \times 10^{-18}$ m$^3$ or not greater than $100 \times 10^{-18}$ m$^3$ for the biomolecule having the low reaction rate. The "hydrophobic material" may be, for example, a hydrophobic resin such as a fluororesin or a hydrophobic non-resin substance such as glass.

In the first high-density micro-chamber array of the above aspect, the plurality of micro-chambers may be formed in a thin film of the hydrophobic material having a thickness of not greater than 10 micrometers to have a diameter in circle equivalent of not larger than 40 micrometers, may be formed in a thin film of the hydrophobic material having a thickness of not greater than 2 micrometers to have a diameter in circle equivalent of not larger than 10 micrometers, or may be formed in a thin film of the hydrophobic material having a thickness of not greater than 1 micrometer to have a diameter in circle equivalent of not larger than 5 micrometers. This configuration forms the high-density micro-chamber array by employing the technique of forming a thin film of a hydrophobic material on the surface of a substrate and subsequently forming a plurality of micro-chambers in the thin film. This can relatively easily provide the high-density chamber array.

In the first high-density micro-chamber array of the above aspect, the plurality of micro-chambers may be formed in a thin film of the hydrophobic material having a thickness in a predetermined thickness range including 500 nanometers to have a diameter in circle equivalent in a predetermined diameter range including 1 micrometer. By taking into account the easiness of manufacture as well as the magnitude of the reaction rate of the biomolecule as the test object and the content rate of the biomolecule, it is thought that the thickness and the diameter of the micro-chamber are preferably several hundred nanometers to several micrometers. The "predetermined thickness range" may be, for example, a range of not less than 50 nanometers that is 0.1-fold of 500 nanometer and not greater than 5 micrometers that is 10-fold of 500 nanometers or a range of not less than 250 nanometers that is 0.5-fold of 500 nanometers and not greater than 1 micrometer that is 2-fold of 500 nanometers. The "predetermined diameter range" may be, for example, a range of not less than 100 nanometers that is 0.1-fold of 1 micrometer and not greater than 10 micrometers that is 10-fold of 1 micrometer or a range of not less than 500 nanometers that is 0.5-fold of 1 micrometer and not greater than 2 micrometers that is 2-fold of 1 micrometer.

In the first high-density micro-chamber array of the above aspect, a membrane protein may be reconstituted in the lipid bilayer membrane. This enables the first high-density micro-chamber array of this aspect to be used for detection of, for example, the reactions of biomolecules via various membrane proteins.

The present invention is also directed to a second high-density micro-chamber array. The second high-density micro-chamber array includes a first micro-chamber member including a flat first substrate, a plurality of first micro-chambers, each having a capacity of not greater than $4000 \times 10^{-18}$ m$^3$, that are formed from a hydrophobic first material on a surface of the first substrate to be arrayed regularly at a high density and a first lipid membrane that is formed at openings of the plurality of first micro-chambers filled with a first aqueous test solution to liquid-seal the first aqueous test solution. The high-density micro-chamber array further includes a second micro-chamber member including a flat second substrate, a plurality of second micro-chambers, each having a capacity of not greater than $4000 \times 10^{-18}$ m$^3$, that are formed from a hydrophobic second material on a surface of the second substrate to be arrayed regularly at a high density and a second lipid membrane that is formed at openings of the plurality of second micro-chambers filled with a second aqueous test solution to liquid-seal the second aqueous test solution. The first micro-chamber member and the second micro-chamber member are joined with each other such that a surface of the first micro-chamber member having the plurality of first micro-chambers formed thereon is in contact with a surface of the second micro-chamber member having the plurality of second micro-chambers formed thereon.

In the second high-density micro-chamber array of this aspect, the first micro-chamber member has the plurality of first micro-chambers, each having the capacity of not greater than $4000 \times 10^{-18}$ m$^3$, that are formed on the surface of the flat first substrate to be arrayed regularly at a high density. The openings of the respective first micro-chambers filled with the first aqueous test solution are liquid-sealed by the first lipid membrane. The second micro-chamber member has the plurality of second micro-chambers, each having the capacity of not greater than $4000 \times 10^{-18}$ m$^3$, that are formed on the surface of the flat second substrate to be arrayed regularly at a high density. The openings of the respective second micro-chambers filled with the second aqueous test solution are liquid-sealed by the second lipid membrane. The first micro-chamber member and the second micro-chamber member are joined with each other such that the surface having the plurality of first micro-chambers formed thereon is in contact with the surface having the plurality of second micro-chambers formed thereon or in other words, such that the first lipid membrane and the second lipid membrane are stacked. The area where the first lipid membrane and the second lipid membrane are stacked is configured as a lipid bilayer membrane. This provides the micro-chamber array in which a large number of chambers of the extremely small capacity that are liquid-sealed by the lipid bilayer membrane are formed on the respective sides of the lipid bilayer membrane. In an application of the second high-density micro-chamber array of this aspect for detection of the reaction of a biomolecule, reducing the capacities of the first micro-chambers and the second micro-chambers to be not greater than $4000 \times 10^{-18}$ m$^3$ decreases the number of biomolecules in each first micro-chamber or in each second micro-chamber. This results in enhancing a change in concentration in the chamber by a reaction of one biomolecule and increasing the detection sensitivity in detection as the change in concentration. Even in the case of an extremely slow reaction of the biomolecule, this enables the reaction of the biomolecule to be detected with high sensitivity. In the array configured to have a large number of micro-chambers formed at a high density, even when the reaction of the biomolecule occurs at a low frequency, the reaction proceeds in any of the chambers. This accordingly enables the reaction of the biomolecule to be detected with high sensitivity. The capacity of the first micro-chamber or the capacity of the second micro-chamber is determined according to the magnitude of a reaction rate of a biomolecule specified as a test object and the content rate of the biomolecule and is preferably not greater than $4000 \times 10^{-18}$ m$^3$ for the biomolecule having the high reaction rate and preferably not greater than $1000 \times 10^{-18}$ m$^3$ or not greater than $100 \times 10^{-18}$ m$^3$ for the biomolecule having the low reaction rate. The "hydrophobic first material" or the "hydrophobic second material" may be, for example, a hydrophobic resin such as a fluororesin or a hydrophobic non-resin substance such as glass.

In the second high-density micro-chamber array of the above aspect, the first substrate and the second substrate may be made of an identical material or may be made of different materials. The first substrate and the second substrate may be formed in an identical shape or may be formed in different shapes. The first micro-chamber and the second micro-chamber may be formed in an identical shape or may be formed in different shapes. The first micro-chambers and the second micro-chambers may be arrayed regularly according to an identical rule or may be arrayed regularly according to different rules. The first micro-chambers and the second micro-chambers may be arrayed at an identical density or may be arrayed at different densities. The first aqueous test solution and the second aqueous test solution may be an identical liquid or may be different liquids. The first lipid membrane and the second lipid membrane may be made of an identical lipid or may be made of different lipids.

In the second high-density micro-chamber array of the above aspect, the plurality of first micro-chambers may be formed in a thin film of the hydrophobic first material having a thickness of not greater than 10 micrometers to have a diameter in circle equivalent of not larger than 40 micrometers, may be formed in a thin film of the hydrophobic first material having a thickness of not greater than 2 micrometers to have a diameter in circle equivalent of not larger than 10 micrometers, or may be formed in a thin film of the hydrophobic first material having a thickness of not greater than 1 micrometer to have a diameter in circle equivalent of not larger than 5 micrometers. The plurality of second micro-chambers may be formed in a thin film of the hydrophobic first material having a thickness of not greater than 10 micrometers to have a diameter in circle equivalent of not larger than 40 micrometers, may be formed in a thin film of the hydrophobic first material having a thickness of not greater than 2 micrometers to have a diameter in circle equivalent of not larger than 10 micrometers, or may be formed in a thin film of the hydrophobic first material having a thickness of not greater than 1 micrometer to have a diameter in circle equivalent of not larger than 5 micrometers. This configuration forms the high-density micro-chamber array by employing the technique of forming a first thin film or a second thin film on the surface of a first substrate or on the surface of a second substrate and forming a plurality of first micro-chambers in the first thin film or forming a plurality of second micro-chambers in the second thin film. This can relatively easily provide the high-density chamber array.

In the second high-density micro-chamber array of the above aspect, the plurality of first micro-chambers may be formed in a thin film of the hydrophobic first material having a thickness in a predetermined first thickness range including 500 nanometers to have a diameter in circle equivalent in a predetermined first diameter range including 1 micrometer. The plurality of second micro-chambers may be formed in a thin film of the hydrophobic first material having a thickness in a predetermined second thickness range including 500 nanometers to have a diameter in circle equivalent in a predetermined second diameter range including 1 micrometer. By taking into account the easiness of manufacture as well as the magnitude of the reaction rate of the biomolecule as the test object and the content rate of the biomolecule, it is thought that the thickness and the diameter of the micro-chamber are preferably several hundred nanometers to several micrometers. The "predetermined first thickness range" or the "predetermined second thickness range" may be, for example, a range of not less than 50 nanometers that is 0.1-fold of 500 nanometer and not greater than 5 micrometers that is 10-fold of 500 nanometers or a range of not less than 250 nanometers that is 0.5-fold of 500 nanometers and not greater than 1 micrometer that is 2-fold of 500 nanometers. The "predetermined first thickness range" and the "predetermined second thickness range" may be an identical range or may be different ranges. The "predetermined first diameter range" or the "predetermined second diameter range" may be, for example, a range of not less than 100 nanometers that is 0.1-fold of 1 micrometer and not greater than 10 micrometers that is 10-fold of 1 micrometer or a range of not less than 500 nanometers that is 0.5-fold of 1 micrometer and not greater than 2 micrometers that is 2-fold of 1 micrometer. The "predetermined first diameter range" and the "predetermined second diameter range" may be an identical range or may be different ranges.

In the second high-density micro-chamber array of the above aspect, a membrane protein may be reconstituted in a lipid bilayer membrane that is obtained by joining the first lipid membrane of the first micro-chamber member with the second lipid membrane of the second micro-chamber member. This enables the second high-density micro-chamber array of this aspect to be used for detection of, for example, the reaction of a biomolecule via the membrane protein.

The present invention is also directed to a manufacturing method of a first high-density micro-chamber array. The manufacturing method of the first high-density micro-chamber array includes a chamber forming process of forming a plurality of micro-chambers, each having a capacity of not greater than $4000 \times 10^{-18}$ m$^3$, from a hydrophobic material on a surface of a flat substrate to be arrayed regularly at a high density and a membrane forming process of forming a lipid bilayer membrane at openings of the plurality of micro-chambers filled with an aqueous test solution to liquid-seal the aqueous test solution.

The manufacturing method of the first high-density micro-chamber array of this aspect provides the high-density micro-chamber in which a large number of chambers of the extremely small capacity that are liquid-sealed by the lipid bilayer membrane are formed at a high density. In an application of the first high-density micro-chamber array manufactured by the method of this aspect for detection of the reaction of a biomolecule, reducing the capacity of the micro-chambers to be not greater than $4000 \times 10^{-18}$ m$^3$ decreases the number of biomolecules in each micro-chamber. This results in enhancing a change in concentration in the chamber by a reaction of one biomolecule and increasing the detection sensitivity in detection as the change in concentration. Even in the case of an extremely slow reaction of the biomolecule, this enables the reaction of the biomolecule to be detected with high sensitivity. In the array configured to have a large number of micro-chambers formed at a high density, even when the reaction of the biomolecule occurs at a low frequency, the reaction proceeds in any of the chambers. This accordingly enables the reaction of the biomolecule to be detected with high sensitivity. The capacity of the micro-chamber is determined according to the magnitude of a reaction rate of a biomolecule specified as a test object and the content rate of the biomolecule and is preferably not greater than $4000 \times 10^{-18}$ m$^3$ for the biomolecule having the high reaction rate and preferably not greater than $1000 \times 10^{-18}$ m$^3$ or not greater than $100 \times 10^{-18}$ m$^3$ for the biomolecule having the low reaction rate. The "hydrophobic material" may be, for example, a hydrophobic resin such as a fluororesin or a hydrophobic non-resin substance such as glass.

In the manufacturing method of the first high-density micro-chamber array of the above aspect, the member forming process causes the aqueous test solution to flow in a liquid passage that has an approximately horizontal bottom surface provided by a surface with the plurality of micro-chambers formed thereon, so as to fill the plurality of micro-chambers with the aqueous test solution causing a lipid-containing organic solvent that contains a lipid for forming the lipid bilayer membrane to flow in the liquid passage, so as to form a first lipid membrane in a state that a hydrophilic group of the lipid faces toward the aqueous test solution in the plurality of micro-chambers, at the openings of the micro-chambers and causes a membrane-forming aqueous solution to flow in the liquid passage, so as to form a second lipid membrane in a state that a hydrophobic group of the lipid faces toward the first lipid membrane to be stacked on the first lipid membrane. This can relatively easily manufacture the first high-density chamber array of the invention.

In the manufacturing method of the first high-density micro-chamber array of the above aspect that causes the aqueous test solution to flow in the liquid passage so as to fill the plurality of micro-chambers with the aqueous test solution, the membrane forming process may comprise filling the plurality of micro-chambers with a protein-containing liquid that is prepared by solubilizing or suspending at least a protein in the aqueous test solution, as the filling the plurality of micro-chambers with the aqueous test solution. Using the protein-containing liquid as the aqueous test solution enables a membrane protein to be reconstituted in the lipid bilayer membrane formed at the openings of the micro-chambers. The high-density micro-chamber array having the membrane protein reconstituted in the lipid bilayer membrane can be used for detection of, for example, the reaction of a biomolecule via the membrane protein. The protein in the protein-containing liquid may be any one of a cell membrane fragment including a membrane protein, a lipid bilayer membrane with a protein embedded therein, a water-soluble protein, a liposome with a protein incorporated therein and a protein solubilized by a surface active agent. The technique employed to incorporate the protein into the lipid bilayer membrane may be, for example, membrane fusion for the liposome and may be, for example, thermal fluctuation for the protein solubilized by the surface active agent.

The manufacturing method of the first high-density micro-chamber array of the above aspect may further comprise a reconstitution process of reconstituting a membrane protein in the lipid bilayer membrane, after the membrane forming process. This provides a high-density micro-chamber array having a membrane protein reconstituted in a lipid bilayer membrane. The high-density micro-chamber array having the membrane protein reconstituted in the lipid bilayer membrane can be used for detection of, for example, the reaction of a biomolecule via the membrane protein. In this aspect, the reconstitution process may comprise introducing any one of a cell membrane fragment including a membrane protein, a lipid bilayer membrane with a protein embedded therein, a water-soluble protein, a liposome with a protein incorporated therein and a protein solubilized by a surface active agent into the lipid bilayer membrane, so as to incorporate the protein into the lipid bilayer membrane and form a membrane protein. The technique employed to incorporate the protein into the lipid bilayer membrane may be, for example, membrane fusion for the liposome and may be, for example, thermal fluctuation for the protein solubilized by the surface active agent.

In the manufacturing method of the first high-density micro-chamber array of the above aspect, the chamber forming process may comprise forming a thin film of the hydrophobic material on the surface of the substrate; forming a resist in a remaining area of a surface of the thin film other than an area where the plurality of micro-chambers are to be formed; forming the plurality of micro-chambers in the thin film by dry etching; and removing the resist. This can relatively easily manufacture the high-density micro-chamber array with high accuracy. Any suitable technique other than dry etching, for example, nanoimprint, may be employed to form the plurality of micro-chambers in the thin film.

The present invention is also directed to a manufacturing method of a second high-density micro-chamber array. The manufacturing method of the second high-density micro-chamber array includes a first micro-chamber member forming process of providing a first micro-chamber member by forming a plurality of first micro-chambers, each having a capacity of not greater than $4000\times10^{-18}$ m$^3$, from a hydrophobic first material on a surface of a flat first substrate to be arrayed regularly at a high density and forming a first lipid membrane at openings of the plurality of first micro-chambers filled with a first aqueous test solution to liquid-seal the first aqueous test solution, a second micro-chamber member forming process of providing a second micro-chamber member by forming a plurality of second micro-chambers, each having a capacity of not greater than $4000\times10^{-18}$ m$^3$, from a hydrophobic second material on a surface of a flat second substrate to be arrayed regularly at a high density and forming a second lipid membrane at openings of the plurality of second micro-chambers filled with a second aqueous test solution to liquid-seal the second aqueous test solution and a joining process of joining the first micro-chamber member with the second micro-chamber member such that a surface of the first micro-chamber member having the plurality of first micro-chambers formed thereon is adjacent to a surface of the second micro-chamber member having the plurality of second micro-chambers formed thereon.

In the manufacturing method of the second high-density micro-chamber array of this aspect, the first micro-chamber member and the second micro-chamber member are joined with each other such that the surface having the plurality of first micro-chambers formed thereon is in contact with the surface having the plurality of second micro-chambers formed thereon or in other words, such that the first lipid membrane and the second lipid membrane are stacked. The area where the first lipid membrane and the second lipid membrane are stacked is configured as a lipid bilayer membrane. This provides the micro-chamber array in which a large number of chambers of the extremely small capacity that are liquid-sealed by the lipid bilayer membrane are formed on the respective sides of the lipid bilayer membrane. In an application of the second high-density micro-chamber array manufactured by the method of this aspect for detection of the reaction of a biomolecule, reducing the capacity of the first micro-chambers and the second micro-chambers to be not greater than $4000\times10^{-18}$ m$^3$ decreases the number of biomolecules in each micro-chamber. This results in enhancing a change in concentration in the chamber by a reaction of one biomolecule and increasing the detection sensitivity in detection as the change in concentration. Even in the case of an extremely slow reaction of the biomolecule, this enables the reaction of the biomolecule to be detected with high sensitivity. In the array configured to have a large number of micro-chambers formed at a high density, even when the reaction of the biomolecule occurs at a low frequency, the reaction proceeds in any of the chambers. This accordingly enables the reaction of the biomolecule to be detected with high sensitivity. The capacities of the first micro-chamber and the second micro-chamber are determined according to the magnitude of a reaction rate of a biomolecule specified as a test object and the content rate of the biomolecule and are preferably not greater than $4000\times10^{-18}$ m$^3$ for the biomolecule having the high reaction rate and preferably not greater than $1000\times10^{-18}$ m$^3$ or not greater than $100\times10^{-18}$ m$^3$ for the biomolecule having the low reaction rate. The "hydrophobic first material" or the "hydrophobic second material" may be, for example, a hydrophobic resin such as a fluororesin or a hydrophobic non-resin substance such as glass.

In the manufacturing method of the second high-density micro-chamber array of the above aspect, the first substrate and the second substrate may be made of an identical material or may be made of different materials. The first substrate and the second substrate may be formed in an identical shape or may be formed in different shapes. The first micro-chamber and the second micro-chamber may be formed in an identical shape or may be formed in different shapes. The first micro-chambers and the second micro-chambers may be arrayed regularly according to an identical rule or may be arrayed regularly according to different rules. The first micro-chambers and the second micro-chambers may be arrayed at an identical density or may be arrayed at different densities. The first aqueous test solution and the second aqueous test solution may be an identical liquid or may be different liquids. The first lipid membrane and the second lipid membrane may be made of an identical lipid or may be made of different lipids.

In the manufacturing method of the second high-density micro-chamber array of the above aspect, the first micro-chamber member forming process causes the first aqueous test solution to flow in a first liquid passage that has an approximately horizontal bottom surface provided by a surface with the plurality of first micro-chambers formed thereon, so as to fill the plurality of first micro-chambers with the first aqueous test solution and causes a first lipid-containing organic solvent that contains a first lipid to flow in the first liquid passage, so as to form the first lipid membrane such as to liquid-seal the openings of the plurality of first micro-chambers filled with the first aqueous test solution by the first lipid membrane in a state that a hydrophilic group of the first lipid faces toward the first aqueous test solution. The second micro-chamber member forming process causes the second aqueous test solution to flow in a second liquid passage that has an approximately horizontal bottom surface provided by a surface with the plurality of second micro-chambers formed thereon, so as to fill the plurality of second micro-chambers with the second aqueous test solution and causes a second lipid-containing organic solvent that contains a second lipid to flow in the second liquid passage, so as to form the second lipid membrane such as to liquid-seal the openings of the plurality of second micro-chambers filled with the second aqueous test solution by the second lipid membrane in a state that a hydrophilic group of the second lipid faces toward the second aqueous test solution. This can relatively easily manufacture the second high-density chamber array of the invention.

In the manufacturing method of the second high-density micro-chamber array of the above aspect, the second micro-chamber member forming process may comprise filling the plurality of second micro-chambers with a protein-containing liquid that is prepared by solubilizing or suspending at least a protein in the second aqueous test solution, as the filling the plurality of second micro-chambers with the second aqueous test solution. Using the protein-containing liquid as the second aqueous test solution enables a membrane protein to be reconstituted in the lipid bilayer membrane. The high-density micro-chamber array having the membrane protein reconstituted in the lipid bilayer membrane can be used for detection of, for example, the reaction of a biomolecule via the membrane protein. The protein in the protein-containing liquid may be any one of a cell membrane fragment including a membrane protein, a lipid bilayer membrane with a protein embedded therein, a water-soluble protein, a liposome with a protein incorporated therein and a protein solubilized by a surface active agent. The technique employed to incorporate the protein into the lipid bilayer membrane may be, for example, membrane fusion for the liposome and may be, for example, thermal fluctuation for the protein solubilized by the surface active agent.

In the manufacturing method of the second high-density micro-chamber array of the above aspect, the first micro-chamber member forming process may comprise forming a first thin film of the first material on the surface of the first substrate; forming a first resist in a remaining area of a surface of the first thin film other than an area where the plurality of first micro-chambers are to be formed; forming the plurality of first micro-chambers in the first thin film by dry etching; and removing the first resist. The second micro-chamber member forming process may comprise forming a second thin film of the second material on the surface of the second substrate; forming a second resist in a remaining area of a surface of the second thin film other than an area where the plurality of second micro-chambers are to be formed; forming the plurality of second micro-chambers in the second thin film by dry etching; and removing the second resist. This can relatively easily manufacture the first micro-chamber member and the second micro-chamber member with high accuracy. Any suitable technique other than dry etching, for example, nanoimprint, may be employed to form the plurality of first micro-chambers in the first thin film and to form the plurality of second micro-chambers in the second thin film.

DESCRIPTION OF EMBODIMENTS

Some aspects of the invention are described with reference to embodiments.

Figure 1:
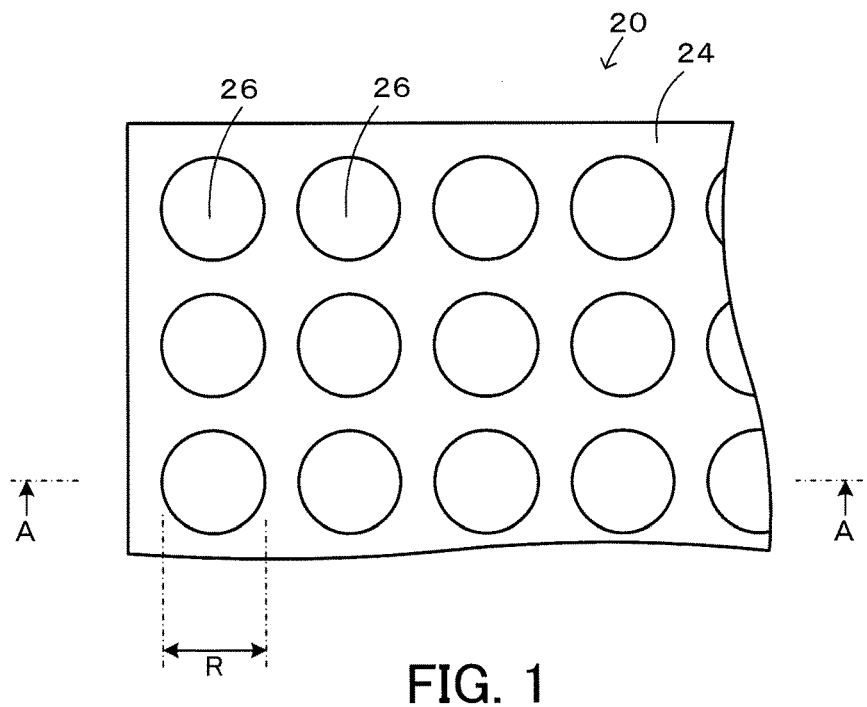
FIG. 1 is a configuration diagram illustrating the schematic configuration of a high-density micro-chamber array 20 according to a first embodiment of the invention.
Figure 2:
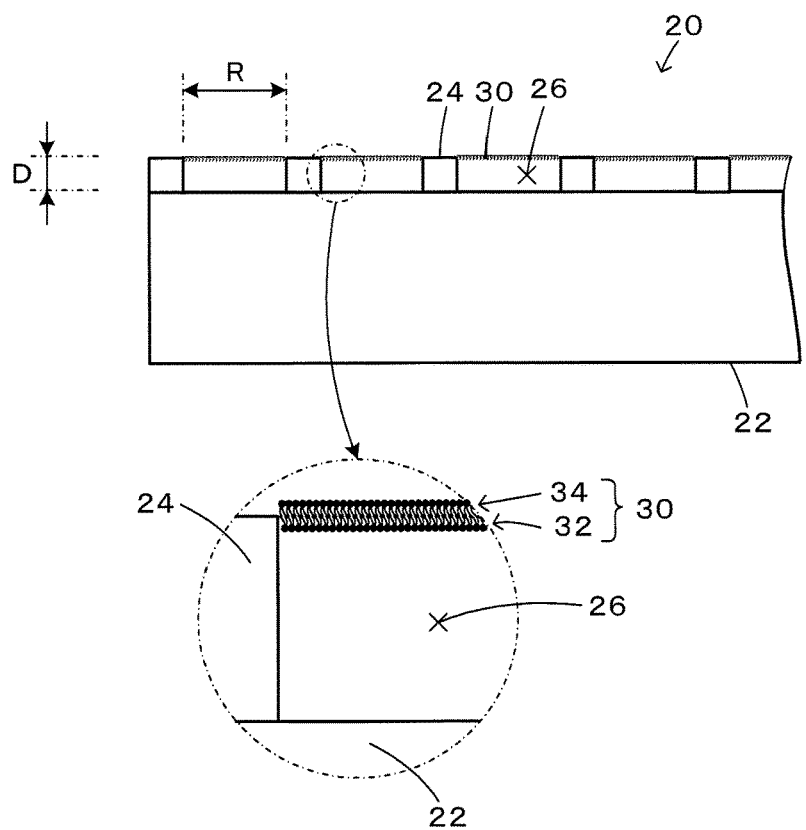
FIG. 2 is a diagram illustrating a section of the high-density micro-chamber array of the first embodiment taken on a line A-A in FIG. 1 and an enlarged view of part of the section.

FIG. 1 is a configuration diagram illustrating the schematic configuration of a high-density micro-chamber array 20 according to a first embodiment of the invention. FIG. 2 is a diagram illustrating a section of the high-density micro-chamber array 20 of the first embodiment taken on a line A-A in FIG. 1 and an enlarged view of part of the section. As shown in FIG. 2, the high-density micro-chamber array 20 of the first embodiment is comprised of a flat glass substrate 22, a material film 24 made of a hydrophobic material (for example, a fluororesin (CYTOP) manufactured by Asahi Glass Co., Ltd.) as a thin film on a surface of the glass substrate 22, a plurality of micro-chambers 26 formed in the material film 24 to be arrayed regularly at a high density, and a lipid bilayer membrane 30 provided to liquid-seal the openings of the respective chambers 26 that are filled with an aqueous test solution.

Each of the micro-chambers 26 is formed in the material film 24 having a thickness D of 1 μm to have a diameter R of 5 μm. Each micro-chamber 26 accordingly has a capacity $L=\pi(2.5\times10^{-6})^2\times1\times10^{-6}$ [m$^3$]≈19.6×10$^{-18}$ [m$^3$]. In a configuration that the micro-chambers 26 are arrayed at intervals of 2 μm both in a vertical direction and in a horizontal direction, an area S required for one micro-chamber 26 is defined by a 7-μm square and is calculated as $S=(7\times10^{-6})^2$ [m$^2$]=49×10$^{-12}$ [m$^2$]. Accordingly, about 2×10$^6$ micro-chambers 26 are formed per 1 cm$^2$ (1×10$^{-4}$ [m$^2$]) on the glass substrate 22.

The lipid bipolar membrane 30 is formed by stacking a first lipid membrane 32 that has a hydrophilic group of a lipid facing toward the micro-chambers 26 (downward in FIG. 2) and a second lipid membrane 34 that has a hydrophobic group of the lipid facing toward the micro-chambers 26 (downward in FIG. 2) such that the hydrophobic group is placed on an inner side. The lipid used to form the first lipid membrane 32 and the second lipid membrane 34 may be a natural lipid such as a soybean-derived lipid or an *Escherichia coli*-derived lipid or an artificial lipid such as DOPE (dioleoylphosphatidylethanolamine) or DOPG (dioleoyl-phosphatidylglycerol).

Figure 3:
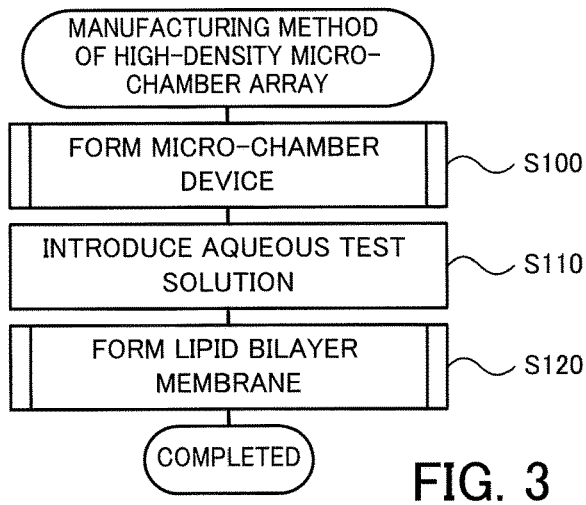
FIG. 3 is a manufacturing process diagram illustrating one example of a manufacturing method of the high-density micro-chamber array 20 according to the first embodiment.
Figure 4:
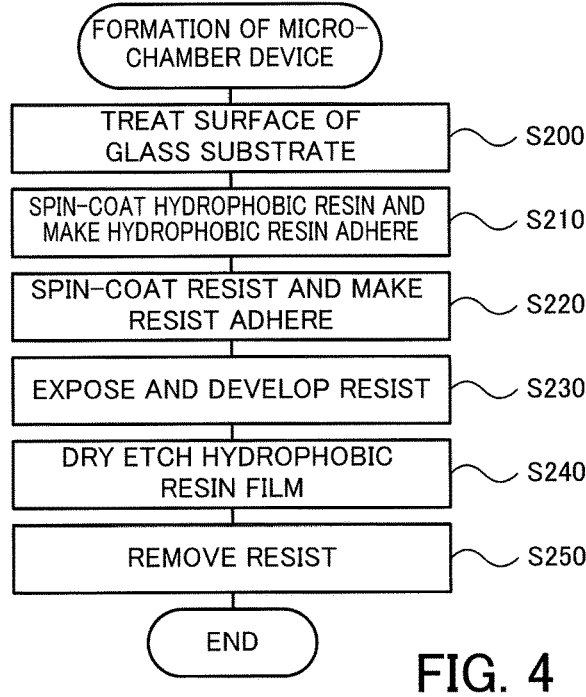
FIG. 4 is a process diagram showing one example of forming a micro-chamber device (process S100)

The following describes manufacture of this high-density micro-chamber array 20 of the first embodiment. FIG. 3 is a manufacturing process diagram illustrating one example of a manufacturing method of the high-density micro-chamber array 20 according to the first embodiment. The manufacturing method of the high-density micro-chamber array 20 of the first embodiment first forms a micro-chamber device in which openings are not liquid-sealed by a lipid bilayer membrane 30 (process S100), introduces an aqueous test solution into the formed micro-chamber device (process S110), and then forms a lipid bilayer membrane 30 to liquid-seal the openings of the respective micro-chambers 26 that are filled with the aqueous test solution (process P120). This completes the high-density micro-chamber array 20. Formation of the micro-chamber device is performed, for example, according to a process diagram shown in FIG. 4, and formation of the lipid bilayer membrane 30 is performed, for example, according to a process diagram shown in FIG. 5. The following sequentially describes the process of forming the micro-chamber device and the process of forming the lipid bilayer membrane 30.

Figure 6:
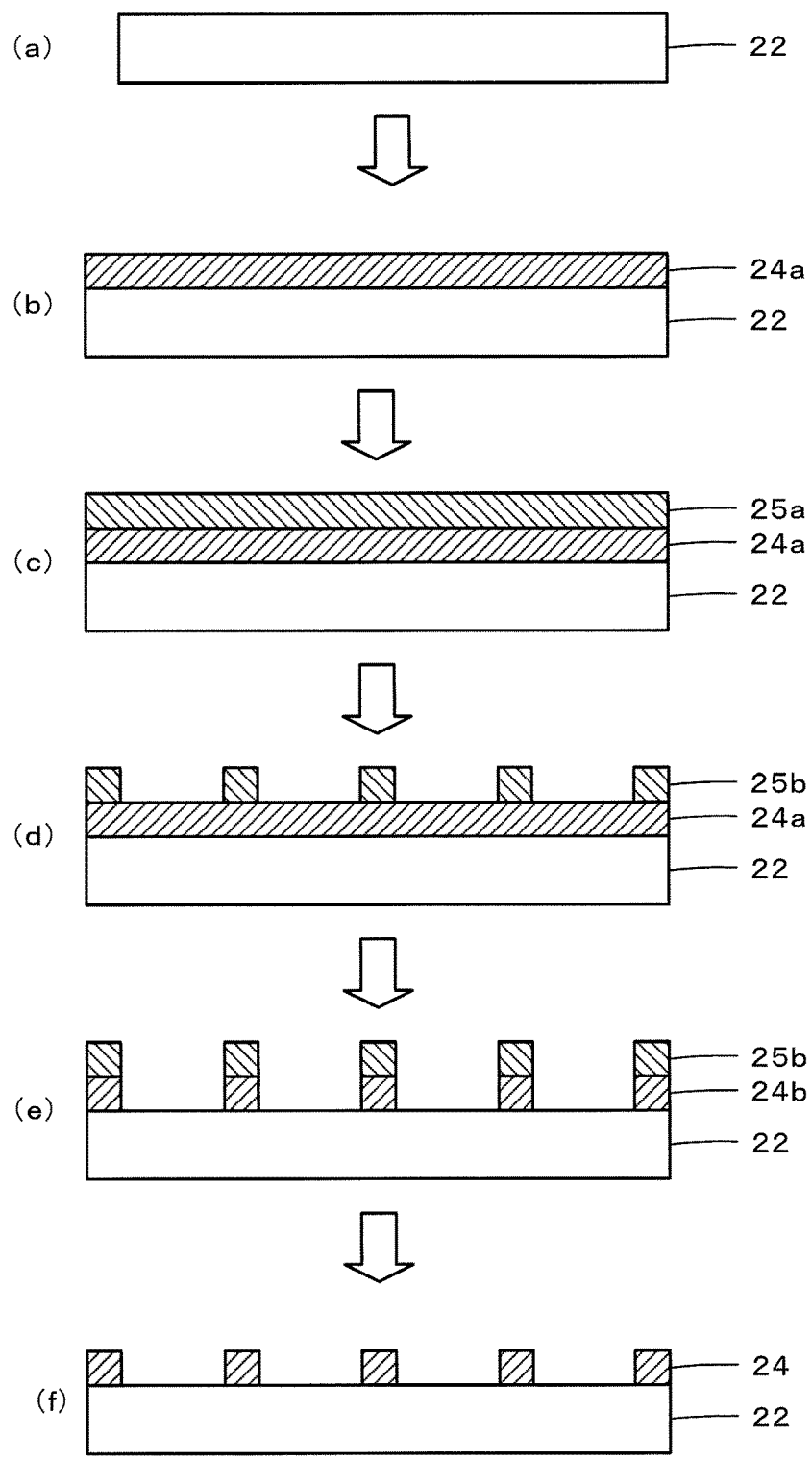
FIG. 6 is diagrams illustrating respective processes in formation of the micro-chamber device.

Formation of the micro-chamber device is described first. FIG. 6 illustrates respective processes in formation of the micro-chamber device. The process of forming the micro-chamber device first soaks the glass substrate 22 in a 10M potassium hydroxide (KOH) solution for about 24 hours as surface treatment to produce hydroxyl group on a glass surface of the glass substrate 22 (process S200, FIG. 6(a)). The process subsequently spin-coats a hydrophobic material (for example, a fluororesin (CYTOP) manufactured by Asahi Glass Co., Ltd.) on the surface of the glass substrate 22 to form a material film 24a and make the material film 24a adhere to the glass surface of the glass substrate 22 (process S210, FIG. 6(b)). The conditions of spin-coating may be, for example, 2000 rps (revolution per second) for 30 seconds. This provides the material film 24a having the film thickness of about 1 μm. The material film 24a may be made to adhere to the glass surface of the glass substrate 22 by, for example, baking the glass substrate 22 with the material film 24a on a hot plate at 180° C. for 1 hour to cause dehydration condensation of the silanol group of the material film 24a (CYTOP) with the hydroxyl group on the glass surface.

After making the material film 24a adhere to the glass surface, the process forms a resist 25a on the surface of the material film 24a by spin-coating and makes the resist 25a adhere to the surface of the material film 24a (process S220, FIG. 6(c)). For example, AZ-4903 manufactured by AZ Electronics Materials may be used for the resist 25a. The conditions of spin-coating may be, for example, 4000 rps (revolution per second) for 60 seconds. The resist 25a may be made to adhere to the surface of the material film 24a by, for example, baking the glass substrate 22 with the resist 25a on a hot plate at 110° C. for 1 hour to cause evaporation of the organic solvent included in the resist 25a.

After making the resist 25a adhere to the surface of the material film 24a, the process exposes the resist 25a using a mask having a pattern of micro-chambers 26 and soaks the resist 25a in a developer exclusive for resist to develop and form a resist 25b with omission of areas where the micro-chambers 26 are to be formed (process S230, FIG. 6(d)). The conditions of exposure may be, for example, irradiation of UV of 250 W power for 7 seconds using an exposure machine manufactured by SAN-EI. The conditions of development may be, for example, soaking in AZ developer manufactured by AZ Electronic Materials for 5 minutes.

The process subsequently dry etches the material film 24a masked by the resist 25b to provide a material film 24b with omission of the areas where the micro-chambers 26 are to be formed from the material film 24a (process S240, FIG. 6(e)) and removes the resist 25b (process S250) to complete the micro-chamber device having the plurality of micro-chambers 26 formed in the material film 24 on the surface of the glass substrate 22. The conditions of dry etching may be, for example, O$_2$ of 50 sccm, pressure of 10 Pa, power of 50 W and time of 30 minutes using a reactive ion etching apparatus manufactured by Samco. The resist 25b may be removed by soaking in acetone, washing with isopropyl alcohol and washing with pure water.

Figure 7:
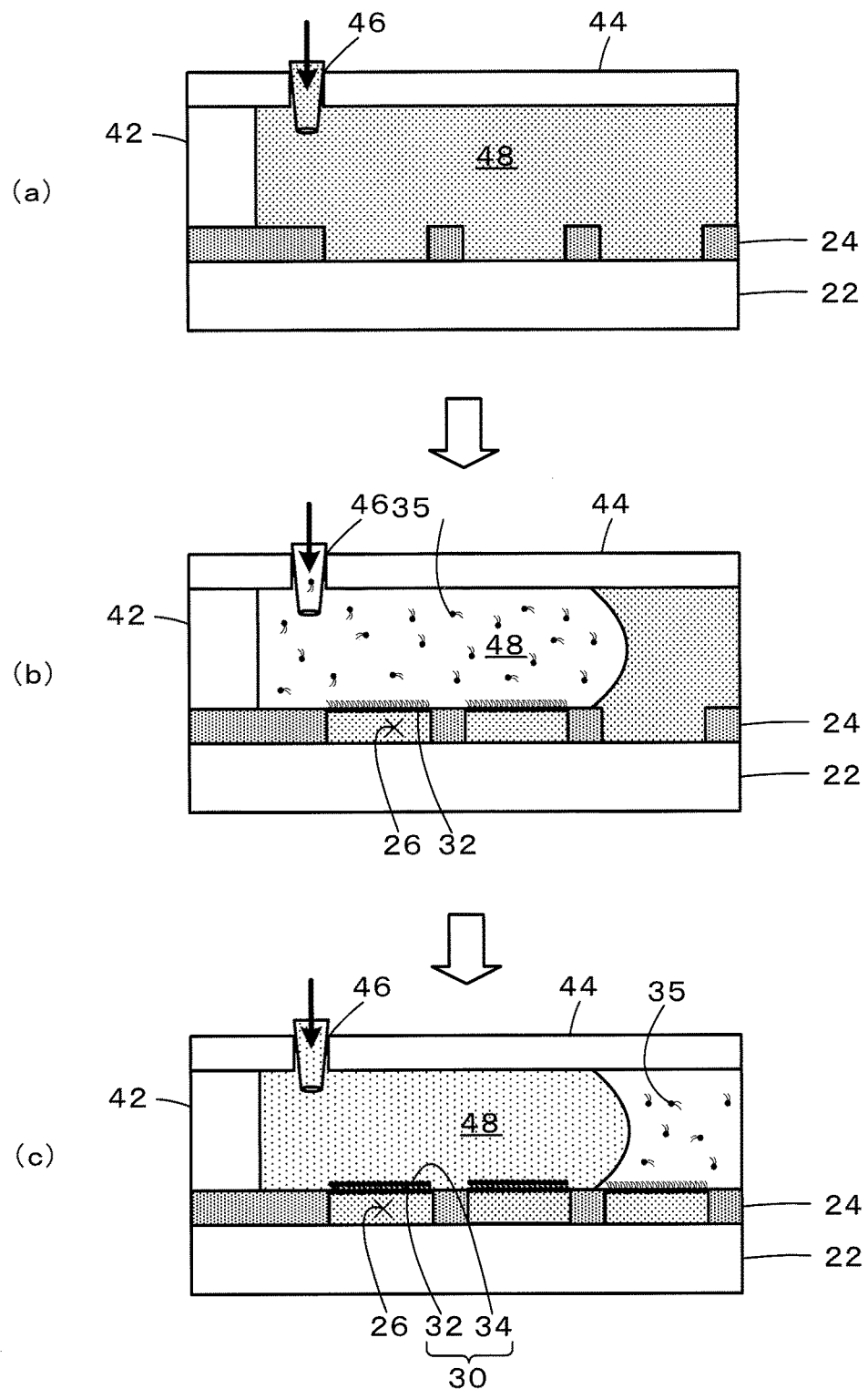
FIG. 7 is diagrams illustrating formation of the lipid bilayer membrane 30.

Formation of the lipid bilayer membrane 30 is described below. FIG. 7 is diagrams illustrating formation of the lipid bilayer membrane 30. A preliminary process prior to forming the lipid bilayer membrane 30 places a glass plate 44 with a liquid inlet port 46 on the micro-chamber device across a spacer 42 to forma liquid passage 48 that has an approximately horizontal bottom surface provided by the surface of the micro-chamber device with the micro-chambers 26 formed thereon, and introduces an aqueous test solution through the liquid inlet port 46 to fill the liquid passage 48 with the aqueous test solution (FIG. 7(a)). The composition of the aqueous test solution may be determined appropriately and may include, for example, a 10 mM pH buffer (pH of 5 to 9), a 20 μM fluorescent indicator (for example, Cal520 or pHrodo) and 10 mM sodium chloride.

Figure 5:
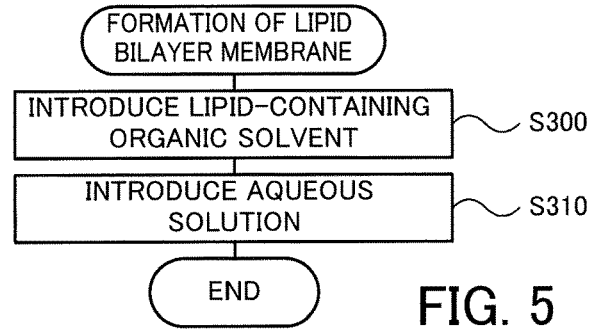
FIG. 5 is a process diagram showing one example of forming a lipid bilayer membrane 30 (process S120)

The process introduces an organic solvent containing a lipid 35 through the liquid inlet port 46 into the liquid passage 48 filled with the aqueous test solution (process S300 in FIG. 5, FIG. 7(b)). The lipid 35 used may be a natural lipid such as a soybean-derived lipid or an *Escherichia coli*-derived lipid or an artificial lipid such as DOPE (dioleoylphosphatidylethanolamine) or DOPG (dioleoylphosphatidylglycerol). The organic solvent used may be hexadecane or chloroform. Introducing the organic solvent containing the lipid 35 causes the openings of the micro-chambers 26 filled with the aqueous test solution to be liquid-sealed by a first lipid membrane 32 in the state that a hydrophilic group of the lipid 35 faces toward the micro-chambers 26.

The process subsequently introduces a membrane-forming aqueous solution for forming the lipid bilayer membrane 30 through the liquid inlet port 46 (process S310 in FIG. 5, FIG. 7(c)) to form the lipid bilayer membrane 30. The composition of the membrane-forming aqueous solution may include, for example, a 10 mM pH buffer (pH of 5 to 9) and 10 mM sodium chloride. The high-density micro-chamber array 20 of the first embodiment is completed by removing the glass plate 44 and the spacer 42 after forming the lipid bilayer membrane 30.

The manufacturing method of the high-density micro-chamber array 20 according to the first embodiment described above can relatively easily manufacture the high-density micro-chamber array 20 in which a large number of the micro-chambers 26 of the extremely small capacity that are liquid-sealed by the lipid bilayer membrane 30 are formed at a high density.

In the high-density micro-chamber array 20 of the first embodiment manufactured as described above, each of the micro-chambers 26 has the extremely small capacity L of $19.6 \times 10^{-18}$ [m$^3$]. In an application of the high-density micro-chamber array 20 of the first embodiment for detection of the reaction of a biomolecule, this configuration decreases the number of biomolecules in the micro-chamber 26. This results in enhancing a change in concentration in the micro-chamber 26 by the reaction of one biomolecule and increasing the detection sensitivity in detection as the change in concentration. Even in the case of an extremely slow reaction of the biomolecule, this enables the reaction of the biomolecule to be detected with high sensitivity. In the array configured to have a large number of the micro-chambers 26 formed at a high density as about $2 \times 10^6$ per 1 cm$^2$ ($1 \times 10^{-4}$ [m$^2$]), even when the reaction of the biomolecule occurs at a low frequency, the reaction proceeds in any of the micro-chambers 26. This accordingly enables the reaction of the biomolecule to be detected with high sensitivity.

Figure 8:
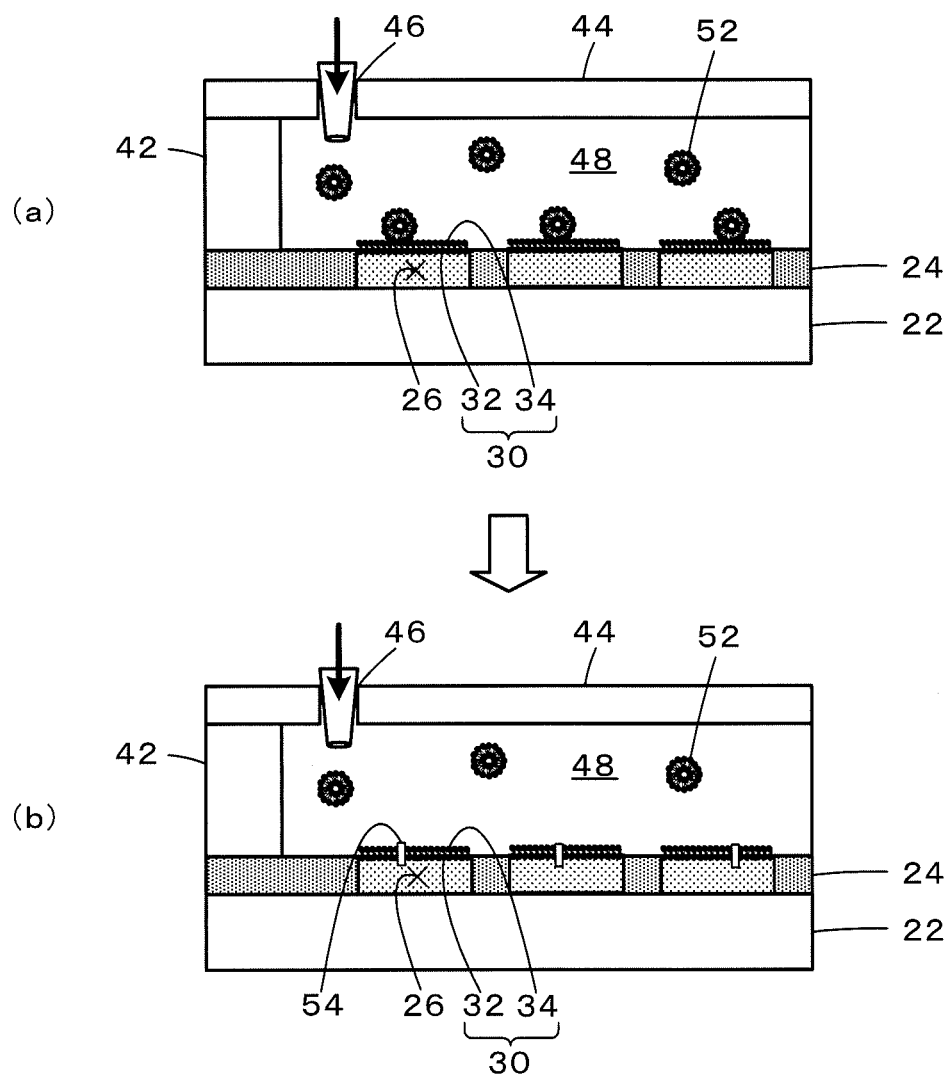
FIG. 8 is diagrams illustrating reconstitution of a membrane protein in the lipid bilayer membrane 30 of the high-density micro-chamber array 20 of the first embodiment.

In the high-density micro-chamber array 20 of the first embodiment described above, a membrane protein may additionally be reconstituted in the lipid bilayer membrane 30. The following describes a procedure of reconstituting a membrane protein in the lipid bilayer membrane 30. FIG. 8 is diagrams illustrating reconstitution of a membrane protein in the lipid bilayer membrane 30 of the high-density micro-chamber array 20 of the first embodiment. The procedure of reconstituting a membrane protein provides the liquid passage 48 formed by placing the glass plate 44 on the micro-chamber device across the spacer 42, introduces a solution of a membrane protein 54 reconstituted in a liposome 52 of 50 μl in volume through the liquid inlet port 46 of the glass plate 44 (FIG. 8(a)) and performs incubation for 1 hour to incorporate the membrane protein 54 into the lipid bilayer membrane 30 by membrane fusion (FIG. 8(b)). The composition of the solution of the membrane protein 54 may include, for example, 10 nM FoF1 (ATP synthase), 1 mM MOPS (3-morpholinopropane-1-sulfonic acid) of pH 7, 10 mM sodium chloride (NaCl) and 2 mM magnesium chloride (MgCl$_2$). Reconstitution of the membrane protein 54 in the lipid bilayer membrane 30 of the high-density micro-chamber array 20 of the first embodiment enables the high-density micro-chamber array 20 of the first embodiment to be used for detection of, for example, the reaction of a biomolecule via the membrane protein. The above description employs the technique of membrane fusion using the liposome to reconstitute the membrane protein in the lipid bilayer membrane 30. Another technique may, however, be employed to reconstitute the membrane protein in the lipid bilayer membrane 30. For example, a membrane protein solubilized by a surface active agent or a water-soluble protein may be introduced to be reconstituted in the lipid bilayer membrane 30. A procedure of reconstituting the membrane protein solubilized by the surface active agent in the lipid bilayer membrane 30 may introduce a membrane protein solution including a membrane protein solubilized by a volume 50 μl of a surface active agent through the liquid inlet port 46 of the glass plate 44 and performs incubation for 1 hour to incorporate the membrane protein into the lipid bilayer membrane 30 by thermal fluctuation. The composition of the membrane protein solution may include, for example, 10 nM FoF1 (ATP synthase), 0.01 to 0.1% n-decyl-β-maltoside (surface active agent), 1 mM MOPS (3-morpholinopropane-1-sulfonic acid) of pH 7, 10 mM sodium chloride (NaCl) and 2 mM magnesium chloride (MgCl$_2$).

A preferable procedure of reconstituting the membrane protein in the lipid bilayer membrane 30 of the high-density micro-chamber array 20 of the first embodiment uses, as the aqueous test solution, a protein-containing liquid prepared by solubilizing or suspending at least a protein in the aqueous test solution in a stage prior to forming the lipid bilayer membrane 30 in the micro-chamber device, i.e., in the process of introducing the aqueous test solution through the liquid inlet port 46 to fill the liquid passage 48 with the aqueous test solution. This procedure introduces the protein-containing liquid as the aqueous test solution through the liquid inlet port 46 to fill the liquid passage 48 with this protein-containing liquid and sequentially introduces the organic solvent containing the lipid 35 and the membrane-forming aqueous solution for forming the lipid bilayer membrane 30 through the liquid inlet port 46 to liquid-seal the openings of the micro-chambers 26 filled with the protein-containing liquid by the lipid bilayer membrane 30. The protein in the protein-containing liquid in the micro-chamber 26 that is liquid-sealed by the lipid bilayer membrane 30 is reconstituted in the lipid bilayer membrane 30 by membrane fusion or thermal fluctuation. The protein in the protein-containing liquid may be a cell membrane fragment including a membrane protein, a lipid bilayer membrane with a protein embedded therein, a water-soluble protein, a liposome with a protein incorporated therein and a protein solubilized by a surface active agent.

Figure 9:
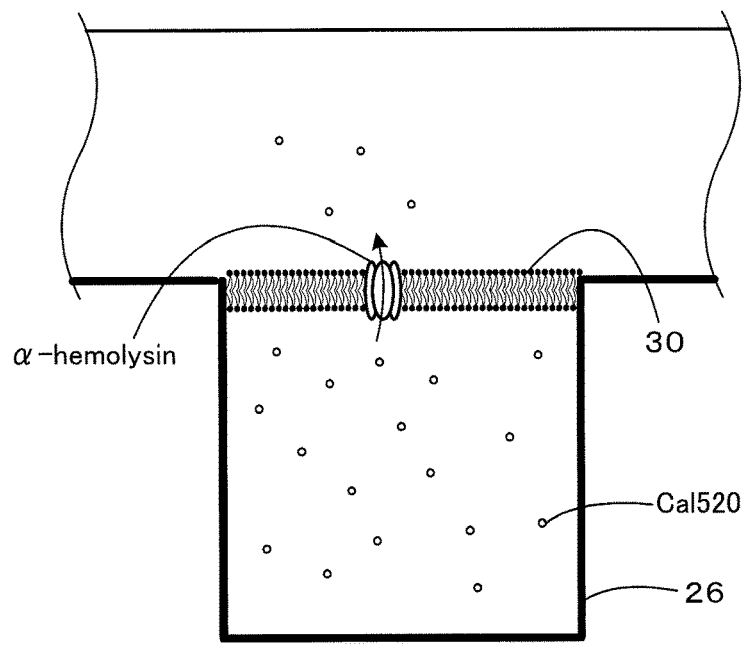
FIG. 9 is a diagram schematically illustrating an experiment of passive transport of a fluorescent dye (Cal520) by α-hemolysin using the high-density micro-chamber array 20 of the first embodiment.
Figure 10:
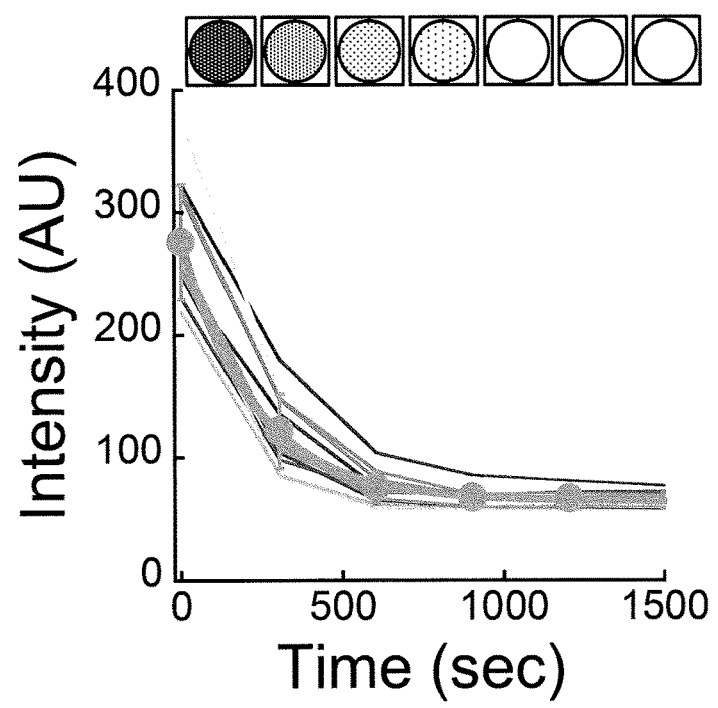
FIG. 10 is a graph showing one example of the results in the experiment of passive transport of the fluorescent dye (Cal520) by α-hemolysin.

FIG. 9 is a schematic diagram illustrating an experiment of passive transport of a fluorescent dye (Cal520) by α-hemolysin using the high-density micro-chamber array 20 of the first embodiment, and FIG. 10 shows the results of this experiment. In this experiment, the aqueous test solution used inside of the micro-chamber 26 was an aqueous solution including 10 mM calcium chloride ($CaCl_2$) and 200 μM calcium indicator (Cal520 (registered trademark). The aqueous solution used outside of the micro-chamber 26 was an aqueous solution of 10 mM calcium chloride ($CaCl_2$). The membrane protein used to be reconstituted in the lipid bilayer membrane 30 was α-hemolysin. In the circles in squares in the upper portion of FIG. 10, the density of color indicates the concentration of the calcium indicator in the micro-chamber 26. As shown in FIG. 10, the concentration of the calcium indicator in the micro-chamber 26 decreases with time.

Figure 11:
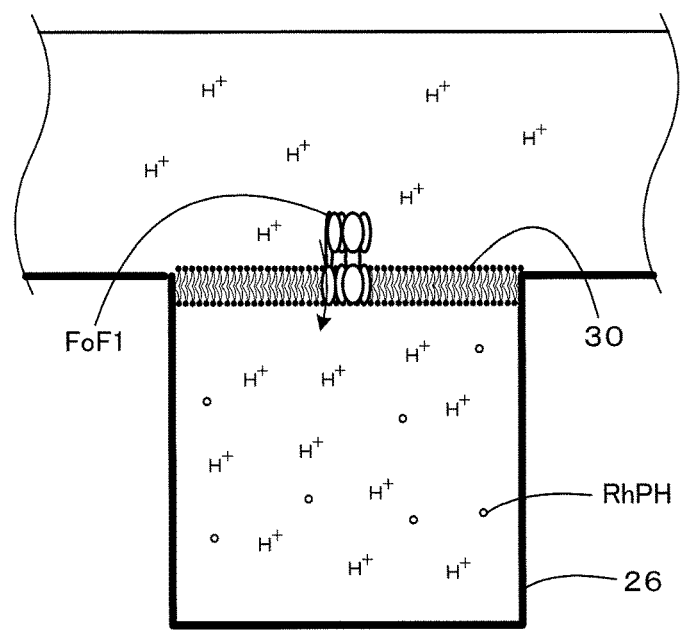
FIG. 11 is a diagram schematically illustrating an experiment of active transport of proton by an F-type ATP synthase (FoF1) using the high-density micro-chamber array 20 of the first embodiment.
Figure 12:
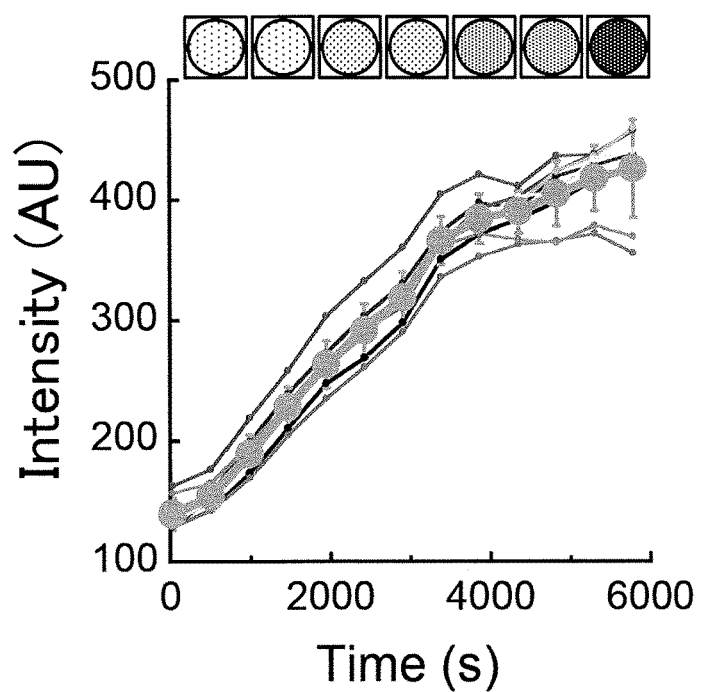
FIG. 12 is a graph showing one example of the results in the experiment of active transport of proton by the F-type ATP synthase (FoF1)

FIG. 11 is a schematic diagram illustrating an experiment of active transport of proton by an F-type ATP synthase (FoF1) using the high-density micro-chamber array 20 of the first embodiment, and FIG. 12 shows the results of this experiment. In this experiment, the aqueous test solution used inside of the micro-chamber 26 was an aqueous solution including 10 μM MOPS (3-morpholinopropane sulfonic acid) buffer (pH 8), 10 mM sodium chloride (NaCl), 10 mM calcium chloride ($CaCl_2$), 2 mM magnesium chloride ($MgCl_2$), 1 μM adenosine diphosphate (ADP) and 20 μM fluorescent pH indicator. The aqueous solution used outside of the micro-chamber 26 was an aqueous solution including 10 μM MOPS (3-morpholinopropane sulfonic acid) buffer (pH 8), 10 mM sodium chloride (NaCl), 10 mM calcium chloride ($CaCl_2$), 2 mM magnesium chloride ($MgCl_2$) and 240 μM adenosine triphosphate (ATP). In the circles in squares in the upper portion of FIG. 12 the density of color indicates the concentration of proton by the fluorescent pH indicator in the micro-chamber 26. As shown in FIG. 12, the concentration of proton in the micro-chamber 26 increases with time.

The high-density micro-chamber array 20 of the first embodiment can be used to detect the reactions of various biomolecules with high sensitivity by changing the combination of the membrane protein to be reconstituted in the lipid bilayer membrane 30, the aqueous test solution inside of the micro-chamber 26 and the aqueous solution outside of the micro-chamber 26, like the experiments described above. In the case where no membrane protein is reconstituted in the lipid bilayer membrane 30, the high-density micro-chamber array 20 of the first embodiment can be used to detect the reactions of various biomolecules via the lipid bilayer membrane 30 with high sensitivity by changing the combination of the aqueous test solution inside of the micro-chamber 26 and the aqueous solution outside of the micro-chamber 26.

In the high-density micro-chamber array 20 of the first embodiment, the micro-chambers 26 are formed in the material film 24 having the thickness D of 1 μm to have the diameter R of 5 μm. The shape and the size of the micro-chamber 26 may be determined appropriately, for example, according to the magnitude of the reaction rate of the biomolecule. For example, micro-chambers may be formed in a material film having the thickness D of 10 μm to have the diameter R of 40 μm. In another example, micro-chambers may be formed in a material film having the thickness D of 2 μm to have the diameter R of 10 μm. The practical and feasible minimum size of micro-chambers is expected to be several hundred nm with regard to both the thickness D of the material film and the diameter R. By taking into account the easiness of manufacture as well as the magnitude of the reaction rate of the biomolecule as the test object and the content rate of the biomolecule, it is thought that the thickness and the diameter of the micro-chamber are practically preferably several hundred nanometers to several micrometers. The micro-chambers may thus be formed to have a thickness in a predetermined thickness range including 500 nanometers and a diameter in circle equivalent in a predetermined diameter range including 1 micrometer. The "predetermined thickness range" should be in the order including 500 nanometers and may be, for example, a range of not less than 50 nanometers that is 0.1-fold of 500 nanometer and not greater than 5 micrometers that is 10-fold of 500 nanometers or a range of not less than 250 nanometers that is 0.5-fold of 500 nanometers and not greater than 1 micrometer that is 2-fold of 500 nanometers. The "predetermined diameter range" should be in the order including 1 micrometer and may be, for example, a range of not less than 100 nanometers that is 0.1-fold of 1 micrometer and not greater than 10 micrometers that is 10-fold of 1 micrometer or a range of not less than 500 nanometers that is 0.5-fold of 1 micrometer and not greater than 2 micrometers that is 2-fold of 1 micrometer. The detection sensitivity to the reaction of a biomolecule is inversely proportional to the number of molecules in the micro-chamber. The practical and feasible maximum capacity L of the micro-chamber to detect the reaction of a biomolecule with high sensitivity is expected to be about $4000 \times 10^{-18}$ [$m^3$]. For example, the result of an experiment using micro-chambers (having the capacity L of $3532.5 \times 10^{-18}$ [$m^3$]) formed in a material film having the thickness of 5 μm to have the diameter R of 30 μm shows the good detection sensitivity to the reaction of the biomolecule. In this case, when the interval between adjacent micro-chambers is set to 4 μm, the area S required for one micro-chamber is defined by a 34 μm square and is calculated as $S=(34 \times 10^{-6})^2$ [$m^2$]$=1156 \times 10^{-12}$ [$m^2$]. Accordingly, about $0.86 \times 10^5$ micro-chambers are formed per 1 $cm^2$ ($1 \times 10^{-4}$ [$m^2$]) on the glass substrate. Even when the reaction of the biomolecule occurs at a low frequency, the reaction proceeds in any of the micro-chambers. This enables the reaction of the biomolecule to be detected with high sensitivity.

In the high-density micro-chamber array 20 of the first embodiment, the fluororesin (CYTOP) manufactured by Asahi Glass Co., Ltd. is used as the material for forming the material film 24. Another hydrophobic resin or a hydrophobic non-resin material (for example, glass) may also be used as this hydrophobic material. In the high-density micro-chamber array 20 of the first embodiment, the material film 24 is formed on the surface of the glass substrate 22, and the micro-chambers are formed in the material film 24. According to a modification, micro-chambers may be formed on the surface of a flat substrate made of a material other than glass, for example, an acrylic resin.

Figure 13:
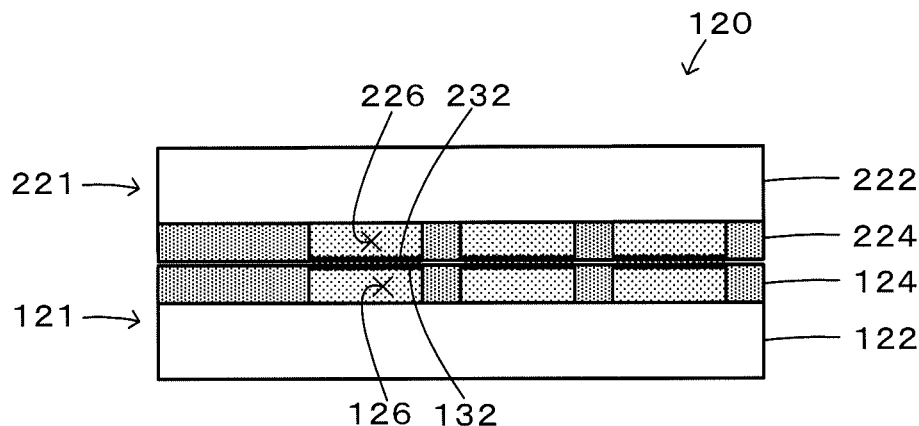
FIG. 13 is a configuration diagram illustrating the schematic configuration of a high-density micro-chamber array 120 according to a second embodiment.

The following describes a high-density micro-chamber array 120 according to a second embodiment of the invention. FIG. 13 is a configuration diagram illustrating the schematic configuration of the high-density micro-chamber array 120 of the second embodiment. As illustrated, the high-density micro-chamber array 120 of the second embodiment is configured by joining two micro-chamber members 121 and 221 in a state similar to the state that the first lipid membrane 32 (FIG. 7(b)) is formed in manufacture of the high-density micro-chamber array 20 of the first embodiment.

The first micro-chamber member 121 is comprised of a flat first glass substrate 122, a first material film 124 made of a hydrophobic material (for example, a fluororesin (CYTOP) manufactured by Asahi Glass Co., Ltd.) as a thin film on a surface of the first glass substrate 122, a plurality of first micro-chambers 126 formed in the first material film 124 to be arrayed regularly at a high density, and a first lipid membrane 132 provided to liquid-seal the openings of the respective first micro-chambers 126 that are filled with a first aqueous test solution. Like the first micro-chamber member 121, the second micro-chamber member 221 is comprised of a flat second glass substrate 222, a second material film 224 made of a hydrophobic material (for example, a fluororesin (CYTOP) manufactured by Asahi Glass Co., Ltd.) as a thin film on a surface of the second glass substrate 222, a plurality of second micro-chambers 226 formed in the second material film 224 to be arrayed regularly at a high density, and a second lipid membrane 232 provided to liquid-seal the openings of the respective second micro-chambers 226 that are filled with a second aqueous test solution. Like the first embodiment, the first aqueous test solution and the second aqueous test solution may be an aqueous solution having the composition including, for example, a 10 mM pH buffer (pH of 5 to 9), a 20 μM fluorescent indicator (for example, Cal520 or pHrodo) and 10 mM sodium chloride. The lipid used to form the first lipid membrane 132 and the second lipid membrane 232 may be a natural lipid such as a soybean-derived lipid or an *Escherichia coli*-derived lipid or an artificial lipid such as DOPE (dioleoylphosphatidylethanolamine) or DOPG (dioleoylphosphatidylglycerol), like the first embodiment.

The first micro-chamber member 121 and the second micro-chamber member 221 are joined with each other such that the surface with the first micro-chambers 126 formed thereon and the surface with the second micro-chambers 226 formed thereon are joint surfaces. Accordingly, the area where the first lipid membrane 132 and the second lipid membrane 232 are stacked by such joining is configured as a lipid bilayer membrane.

The first micro-chamber member 121 and the second micro-chamber member 221 may be formed in a shape similar to that of the high-density micro-chamber array 20 of the first embodiment. More specifically, the first micro-chambers 126 and the second micro-chambers 226 may be formed respectively in a circular shape having the diameter R of 5 μm in the first material film 124 and in the second material film 224 having the thickness D of 1 μm. The first micro-chamber member 121 and the second micro-chamber member 221 may be joined with each other such that the first micro-chambers 126 and the second micro-chambers 226 are aligned. This configuration causes the first lipid membrane 132 and the second lipid membrane 232 to be entirely overlapped with each other to form a lipid bilayer membrane.

Figure 14:
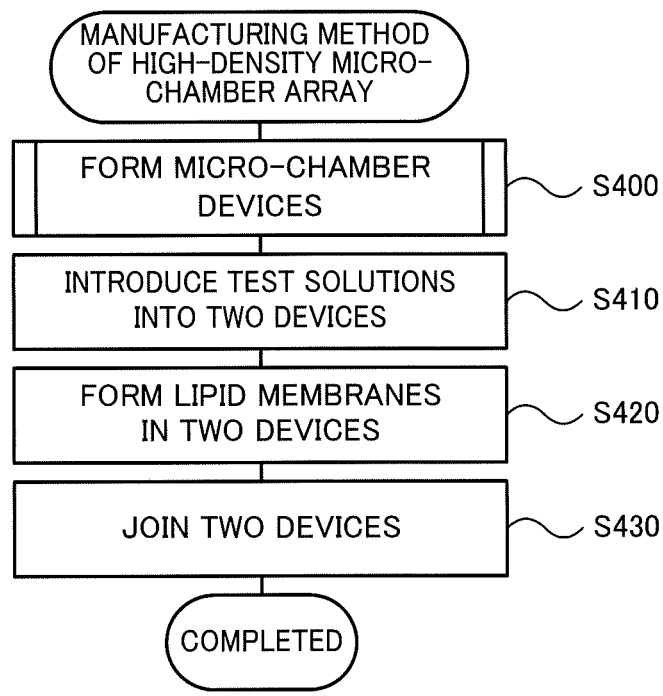
FIG. 14 is a manufacturing process diagram illustrating one example of a manufacturing method of the high-density micro-chamber array 120 according to the second embodiment.
Figure 15:
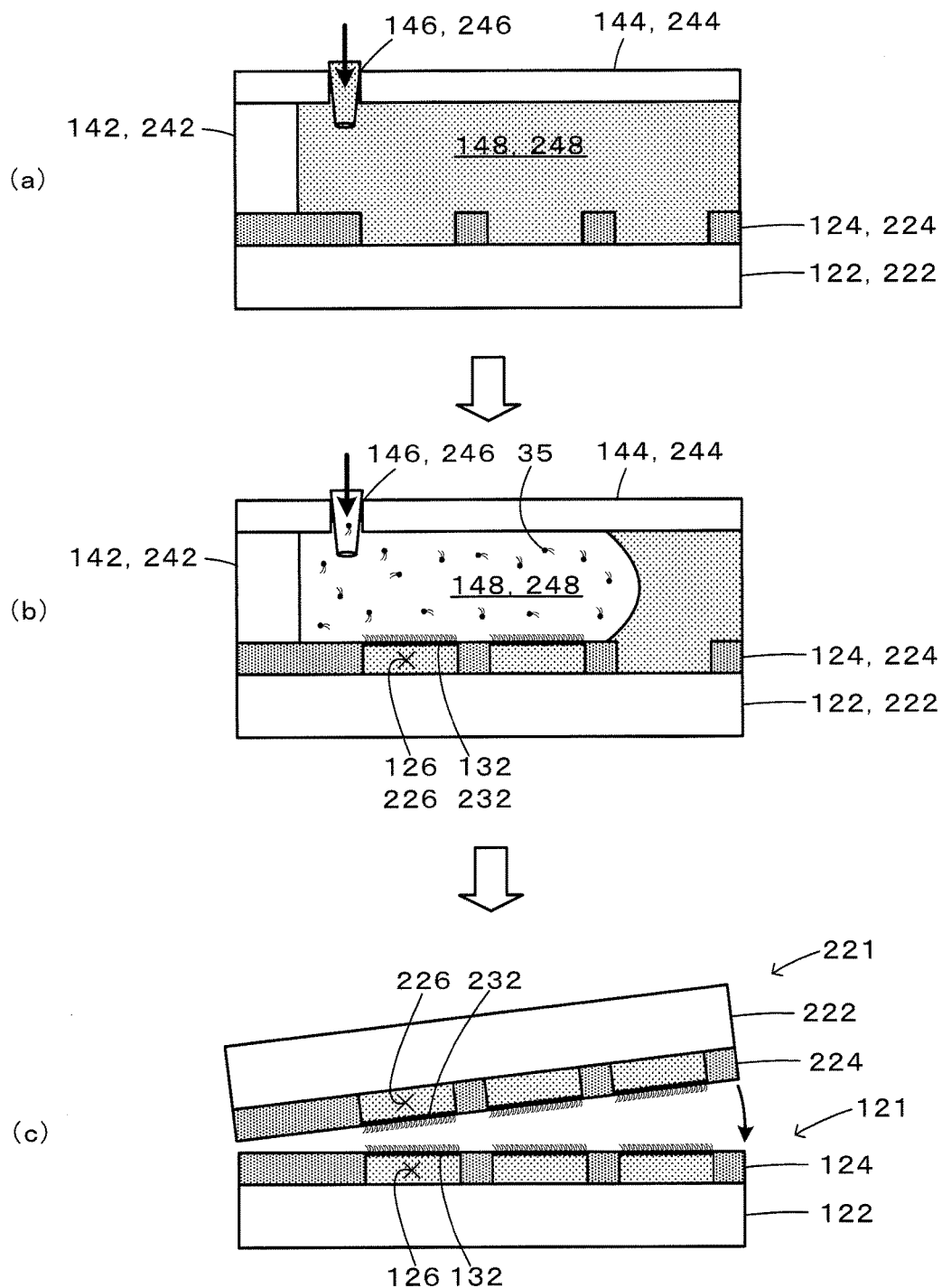
FIG. 15 is diagrams illustrating respective processes in manufacture of the high-density micro-chamber array 120 of the second embodiment.

The following describes a manufacturing method of the high-density micro-chamber array 120 according to the second embodiment. FIG. 14 is a manufacturing process diagram illustrating one example of a manufacturing method of the high-density micro-chamber array 120 of the second embodiment. FIG. 15 is diagrams illustrating respective processes in manufacture of the high-density micro-chamber array 120 of the second embodiment. The procedure of manufacturing the high-density micro-chamber array 120 of the second embodiment first forms two micro-chamber devices (process S400). Formation of the micro-chamber device is described in detail above with regard to the first embodiment. The procedure subsequently places glass plates 144 and 244 with liquid inlet ports 146 and 246 on the respective two micro-chamber devices across spacers 142 and 242 to form liquid passages 148 and 248 in the micro-chamber devices and introduces the first aqueous test solution through the liquid inlet port 146 of one micro-chamber device into the liquid passage 148 while introducing the second aqueous test solution through the liquid inlet port 246 of the other micro-chamber device into the liquid passage 248 (process S410, FIG. 15(*a*)).

With regard to the micro-chamber device in which the first aqueous test solution is introduced, the procedure subsequently introduces an organic solvent containing a lipid 35 through the liquid inlet port 146 in the state that the respective first micro-chambers 126 are filled with the first aqueous test solution, so as to form the first lipid membrane 132 at the openings of the respective first micro-chambers 126 in the state that a hydrophilic group faces toward the first micro-chambers 126. With regard to the micro-chamber device in which the second aqueous test solution is introduced, the procedure subsequently introduces an organic solvent containing the lipid 35 through the liquid inlet port 246 in the state that the respective second micro-chambers 226 are filled with the second aqueous test solution, so as to form the second lipid membrane 132 at the openings of the respective second micro-chambers 226 in the state that a hydrophilic group faces toward the second micro-chambers 226 (process S420, FIG. 15(*b*)). The lipid 35 used may be a natural lipid such as a soybean-derived lipid or an *Escherichia coli*-derived lipid or an artificial lipid such as DOPE (dioleoylphosphatidylethanolamine) or DOPG (dioleoylphosphatidylglycerol). The organic solvent used may be hexadecane or chloroform.

The procedure then joins the first micro-chamber member 121 and the second micro-chamber member 221 with each other such that the surface with the first micro-chambers 126 formed thereon and the surface with the second micro-chambers 226 formed thereon are the joint surfaces (process S430, FIG. 15(*c*)). This completes the high-density micro-chamber array 120 of the second embodiment.

The manufacturing method of the high-density micro-chamber array 120 according to the second embodiment described above can relatively easily manufacture the high-density micro-chamber array 120 of the second embodiment in which a large number of the first micro-chambers 126 and a large number of the second micro-chambers 226 of the extremely small capacity that are liquid-sealed by the lipid bilayer membrane are formed at a high density on the respective sides of the lipid bilayer membrane.

In the high-density micro-chamber array 120 of the second embodiment manufactured as described above, each of the first micro-chambers 126 and the second micro-chambers 226 has the extremely small capacity L of $19.6 \times 10^{-18}$ [$m^3$]. In an application of the high-density micro-chamber array 120 of the second embodiment for detection of the reaction of a biomolecule, this configuration decreases the number of biomolecules in both or either one of the first micro-chamber 126 and the second micro-chamber 226. This results in enhancing a change in concentration in both or either one of the first micro-chamber 126 and the second micro-chamber 226 by the reaction of one biomolecule and increasing the detection sensitivity in detection as the change in concentration. Even in the case of an extremely slow reaction of the biomolecule, this enables the reaction of the biomolecule to be detected with high sensitivity. In the array configured to have a large number of the first micro-chambers 126 and the second micro-chambers 226 formed at a high density as about $2 \times 10^6$ per 1 $cm^2$ ($1 \times 10^{-4}$ [$m^2$]), even when the reaction of the biomolecule occurs at a low frequency, the reaction proceeds in any of the first micro-chambers 126 and the second micro-chambers 226. This accordingly enables the reaction of the biomolecule to be detected with high sensitivity.

Figure 16:
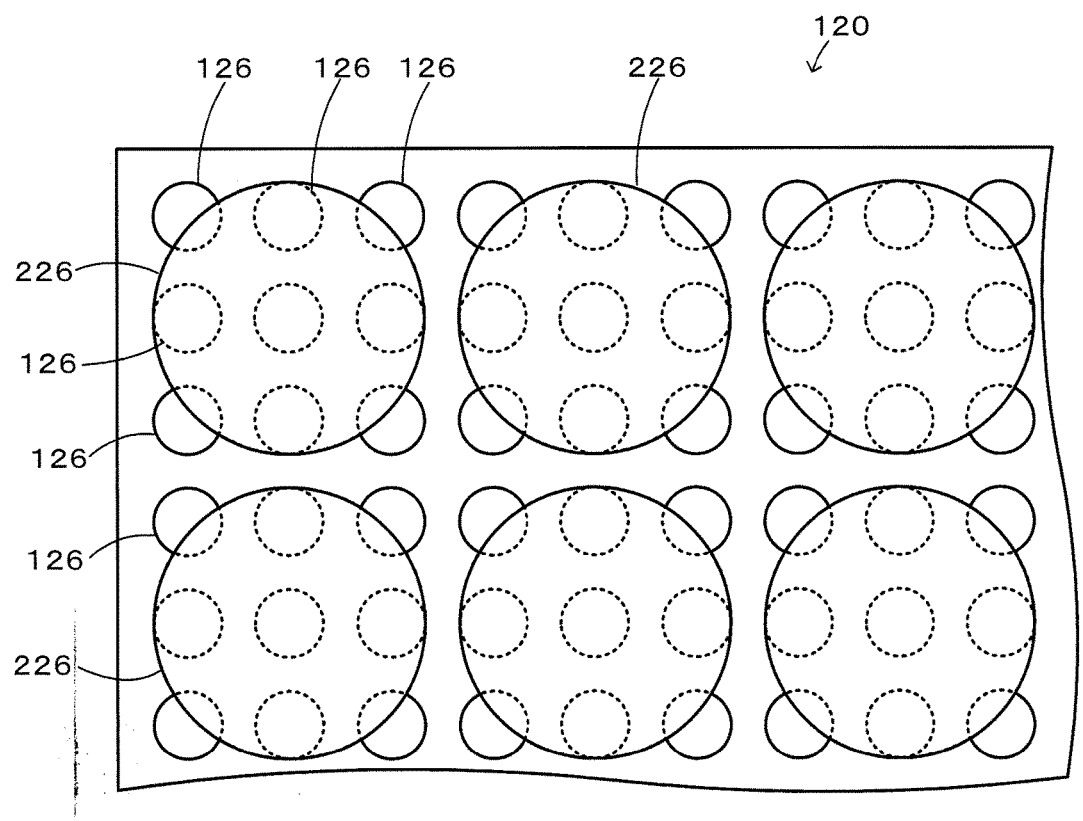
FIG. 16 is a schematic diagram schematically illustrating the high-density micro-chamber array 120 of the second embodiment in which second micro-chambers 226 and first micro-chambers 126 are formed in different sizes.

FIG. 16 schematically illustrates the high-density micro-chamber array 120 of the second embodiment in which the first micro-chambers 126 and the second micro-chambers 226 are formed in different sizes. In this illustrated example, the diameter of the second micro-chambers 226 is approximately 4-fold of the diameter of the first micro-chambers 126. Broken lines in the drawing indicate the areas of the first micro-chambers 126 that are overlapped with the second micro-chambers 226. As described above, the first micro-chambers 126 are liquid-sealed by the first lipid membrane 132, and the second micro-chambers 226 are liquid-sealed by the second lipid membrane 232. Accordingly, the areas where the first micro-chambers 126 are overlapped with the second micro-chambers 226 are configured as the lipid bilayer membrane. With regard to the first micro-chamber member 121, a first aqueous test solution of an identical composition is liquid sealed in all the first micro-chambers 126 by the first lipid membrane 132. With regard to the second micro-chamber member 221, second aqueous test solutions of different compositions are liquid sealed in respective blocks (for example, every 10 lines or every 20 lines) of the second micro-chambers 226 by the second lipid membrane. The high-density micro-chamber array 120 is then formed by joining the first micro-chamber member 121 with the second micro-chamber member 221. In the formed high-density micro-chamber array 120, the second aqueous test solutions of the different compositions filled in the respective blocks of the second micro-chambers 226 may be used to detect different reactions of biomolecules.

In the high-density micro-chamber array 120 of the second embodiment described above, a membrane protein may additionally be reconstituted in the lipid bilayer membrane, as in the high-density micro-chamber array 20 of the first embodiment. A procedure of reconstituting the membrane protein in the lipid bilayer membrane of the high-density micro-chamber array 120 of the second embodiment may use, as the second aqueous test solution, a protein-containing liquid prepared by solubilizing or suspending at least a protein in the second aqueous test solution, in the process of introducing the second aqueous test solution into the other micro-chamber device to fill the liquid passage 248 with the second aqueous test solution. This procedure introduces the protein-containing liquid as the second aqueous test solution through the liquid inlet port 246 to fill the liquid passage 248 with this protein-containing liquid and subsequently introduces the organic solvent containing the lipid 35 through the liquid inlet port 246 to liquid-seal the openings of the second micro-chambers 226 filled with the protein-containing liquid by the second lipid membrane 232. The protein in the protein-containing liquid in the second micro-chamber 226 that is liquid-sealed by the second lipid membrane 232 is reconstituted by membrane fusion or thermal fluctuation in the lipid bilayer membrane that is formed by stacking the first lipid membrane 132 and the second lipid membrane 232. Like the first embodiment, the protein in the protein-containing liquid may be a cell membrane fragment including a membrane protein, a lipid bilayer membrane with a protein embedded therein, a water-soluble protein, a liposome with a protein incorporated therein and a protein solubilized by a surface active agent. Reconstitution of the membrane protein in the lipid bilayer membrane of the high-density micro-chamber array 120 of the second embodiment enables the high-density micro-chamber array 120 of the second embodiment to be used for detection of, for example, the reaction of a biomolecule via the membrane protein.

In the high-density micro chamber array 120 of the second embodiment, the first micro-chamber member 121 and the second micro-chamber member 221 are formed from the same material in the same shape. The first micro-chamber member 121 and the second micro-chamber member 221 may, however, be formed from different materials in different shapes. For example, the first glass substrate 122 and the second glass substrate 222 may be made of an identical material or may be made of different materials. The first glass substrate 122 and the second glass substrate 222 may be formed in an identical shape or may be formed in different shapes. The first material film 124 and the second material film 224 may be made of an identical material or may be made of different materials. The first micro-chamber 126 and the second micro-chamber 226 may be formed in an identical shape or may be formed in different shapes. The first micro-chambers 126 and the second micro-chambers 226 may be arrayed regularly according to an identical rule or may be arrayed regularly according to different rules. Additionally, the first micro-chambers 126 and the second micro-chambers 226 may be arrayed at an identical density or may be arranged at different densities. The first aqueous test solution and the second aqueous test solution may be an identical liquid or may be different liquids. The first lipid membrane 132 and the second lipid membrane 232 may be made of an identical lipid or may be made of different lipids.

In the high-density micro-chamber array 120 of the second embodiment, the first micro-chambers 126 and the second micro-chambers 226 are formed in the first material film 124 and in the second material film 224 having the thickness D of 1 μm to have the diameter R of 5 μm. Like the first embodiment, the shape and the size of the first micro-chamber 126 and the second micro-chamber 226 may be determined appropriately, for example, according to the magnitude of the reaction rate of the biomolecule. For example, the first micro-chambers 126 and the second micro-chambers 226 may be formed in a material film having the thickness D of 10 μm to have the diameter R of 40 μm. In another example, the first micro-chambers 126 and the second micro-chambers 226 may be formed in a material film having the thickness D of 2 μm to have the diameter R of 10 μm. The practical and feasible minimum size of the first micro-chambers 126 and the second micro-chambers 226 is expected to be several hundred nm with regard to both the thickness D of the material film and the diameter R. By taking into account the easiness of manufacture as well as the magnitude of the reaction rate of the biomolecule as the test object and the content rate of the biomolecule, it is thought that the thickness and the diameter of the first micro-chamber 126 and the second micro-chambers 226 are practically preferably several hundred nanometers to several micrometers, like the first embodiment. The first micro-chambers 126 and the second micro-chambers 226 may thus be formed to have a thickness in a predetermined thickness range including 500 nanometers and a diameter in circle equivalent in a predetermined diameter range including 1 micrometer. The "predetermined thickness range" should be in the order including 500 nanometers and may be, for example, a range of not less than 50 nanometers that is 0.1-fold of 500 nanometer and not greater than 5 micrometers that is 10-fold of 500 nanometers or a range of not less than 250 nanometers that is 0.5-fold of 500 nanometers and not greater than 1 micrometer that is 2-fold of 500 nanometers. The "predetermined diameter range" should be in the order including 1 micrometer and may be, for example, a range of not less than 100 nanometers that is 0.1-fold of 1 micrometer and not greater than 10 micrometers that is 10-fold of 1 micrometer or a range of not less than 500 nanometers that is 0.5-fold of 1 micrometer and not greater than 2 micrometers that is 2-fold of 1 micrometer. Like the first embodiment, the practical and feasible maximum capacity L of the first micro-chamber 126 or the second micro-chamber 226 to detect the reaction of a biomolecule with high sensitivity is expected to be about $4000 \times 10^{-18}$ [$m^3$].

In the high-density micro-chamber array 120 of the second embodiment, the fluororesin (CYTOP) manufactured by Asahi Glass Co., Ltd. is used as the material for forming the first material film 124 and the second material film 224. Another hydrophobic resin or a hydrophobic non-resin material (for example, glass) may also be used as this hydrophobic material.

The aspect of the invention is described above with reference to the embodiment. The invention is, however, not limited to the above embodiment but various modifications and variations may be made to the embodiment without departing from the scope of the invention.

INDUSTRIAL APPLICABILITY

The prevent invention is applicable in, for example, manufacturing industries of high-density micro-chamber array.

The invention claimed is:

1. A high-density micro-chamber array, comprising:
   a first micro-chamber member comprising:
      a flat first substrate;
      a plurality of first micro-chambers, each having a capacity of not greater than $4000 \times 10^{-18}$ $m^3$, that are formed from a hydrophobic first material, and are arrayed regularly at a density of about $2 \times 10^6$ per 1 $cm^2$ on a surface of the first substrate; and
      a first lipid membrane that is formed at openings of the plurality of first micro-chambers filled with a first aqueous test solution to liquid-seal the first aqueous test solution; and
   a second micro-chamber member comprising:
      a flat second substrate;
      a plurality of second micro-chambers, each having a capacity of not greater than $4000 \times 10^{-18}$ $m^3$, that are formed from a hydrophobic second material, and are arrayed regularly at density of about $2 \times 10^6$ per 1 $cm^2$ on a surface of the second substrate; and
      a second lipid membrane that is formed at openings of the plurality of second micro-chambers filled with a second aqueous test solution to liquid-seal the second aqueous test solution, wherein
   the first micro-chamber member and the second micro-chamber member are joined with each other such that the first lipid membrane and the second lipid membrane are stacked and configured as a lipid bilayer membrane.

2. The high-density micro-chamber array according to claim 1,
   wherein the plurality of first micro-chambers are formed in a thin film of the hydrophobic first material having a thickness of not greater than 10 micrometers, and
   the plurality of second micro-chambers are formed in a thin film of the hydrophobic second material having a thickness of not greater than 10 micrometers.

3. The high-density micro-chamber array according to claim 2,
   wherein the plurality of first micro-chambers and the plurality of second micro-chambers are formed in different shapes.

4. The high-density micro-chamber array according to claim 2,
   wherein a membrane protein is reconstituted in the lipid bilayer membrane.

5. A manufacturing method of a high-density micro-chamber array according to claim 1, comprising:
   a first micro-chamber member forming process of providing a first micro-chamber member by forming a plurality of first micro-chambers, each having a capacity of not greater than $4000 \times 10^{-18}$ $m^3$, from a hydrophobic first material on a surface of a flat first substrate to be arrayed regularly at a high density and forming a first lipid membrane at openings of the plurality of first micro-chambers filled with a first aqueous test solution to liquid-seal the first aqueous test solution;
   a second micro-chamber member forming process of providing a second micro-chamber member by forming a plurality of second micro-chambers, each having a capacity of not greater than $4000 \times 10^{-18}$ $m^3$, from a hydrophobic second material on a surface of a flat second substrate to be arrayed regularly at a high density and forming a second lipid membrane at openings of the plurality of second micro-chambers filled with a second aqueous test solution to liquid-seal the second aqueous test solution; and
   a joining process of joining the first micro-chamber member with the second micro-chamber member such that a surface of the first micro-chamber member having the plurality of first micro-chambers formed thereon is adjacent to a surface of the second micro-chamber member having the plurality of second micro-chambers formed thereon.

6. The manufacturing method of the high-density micro-chamber array according to claim 5,
   wherein the first micro-chamber member forming process comprises:
   causing the first aqueous test solution to flow in a first liquid passage that has an approximately horizontal bottom surface provided by a surface with the plurality of first micro-chambers formed thereon, so as to fill the plurality of first micro-chambers with the first aqueous test solution; and
   causing a first lipid-containing organic solvent that contains a first lipid to flow in the first liquid passage, so as to form the first lipid membrane such as to liquid-seal the openings of the plurality of first micro-chambers filled with the first aqueous test solution by the first lipid membrane in a state that a hydrophilic group of the first lipid faces toward the first aqueous test solution, and
   the second micro-chamber member forming process comprises:
   causing the second aqueous test solution to flow in a second liquid passage that has an approximately horizontal bottom surface provided by a surface with the plurality of second micro-chambers formed thereon, so as to fill the plurality of second micro-chambers with the second aqueous test solution; and
   causing a second lipid-containing organic solvent that contains a second lipid to flow in the second liquid passage, so as to form the second lipid membrane such as to liquid-seal the openings of the plurality of second micro-chambers filled with the second aqueous test solution by the second lipid membrane in a state that a hydrophilic group of the second lipid faces toward the second aqueous test solution.

7. The manufacturing method of the high-density micro-chamber array according to claim 6,
wherein the second micro-chamber member forming process comprises filling the plurality of second micro-chambers with a protein-containing liquid that is prepared by solubilizing or suspending at least a protein in the second aqueous test solution, as the filling the plurality of second micro-chambers with the second aqueous test solution.

8. The manufacturing method of the high-density micro-chamber array according to claim 7,
wherein the protein in the protein-containing liquid is any one of a cell membrane fragment including a membrane protein, a lipid bilayer membrane with a protein embedded therein, a water-soluble protein, a liposome with a protein incorporated therein and a protein solubilized by a surface active agent.

9. The manufacturing method of the high-density micro-chamber array according to claim 6,
wherein the first micro-chamber member forming process comprises:
forming a first thin film of the first material on the surface of the first substrate;
forming a first resist in a remaining area of a surface of the first thin film other than an area where the plurality of first micro-chambers are to be formed;
forming the plurality of first micro-chambers in the first thin film by dry etching; and
removing the first resist, and
the second micro-chamber member forming process comprises:
forming a second thin film of the second material on the surface of the second substrate;
forming a second resist in a remaining area of a surface of the second thin film other than an area where the plurality of second micro-chambers are to be formed;
forming the plurality of second micro-chambers in the second thin film by dry etching; and
removing the second resist.

* * * * *